United States Patent
Tsunoda

(10) Patent No.: US 11,730,637 B2
(45) Date of Patent: Aug. 22, 2023

(54) DISPOSABLE WEARABLE ARTICLE

(71) Applicant: Daio Paper Corporation, Ehime (JP)

(72) Inventor: Arika Tsunoda, Tochigi (JP)

(73) Assignee: Daio Paper Corporation, Ehime (JP)

( * ) Notice: Subject to any disclaimer, the term of this patent is extended or adjusted under 35 U.S.C. 154(b) by 0 days.

(21) Appl. No.: 18/080,453

(22) Filed: Dec. 13, 2022

(65) Prior Publication Data

US 2023/0181387 A1 Jun. 15, 2023

Related U.S. Application Data

(63) Continuation of application No. 16/607,248, filed as application No. PCT/JP2018/017398 on May 1, 2018, now Pat. No. 11,529,265.

(30) Foreign Application Priority Data

Jul. 19, 2017 (JP) ................................. 2017-140223

(51) Int. Cl.
*B32B 3/24* (2006.01)
*B32B 5/24* (2006.01)
(Continued)

(52) U.S. Cl.
CPC ........ *A61F 13/496* (2013.01); *A61F 13/4902* (2013.01); *A61F 13/49011* (2013.01);
(Continued)

(58) Field of Classification Search
None
See application file for complete search history.

(56) References Cited

U.S. PATENT DOCUMENTS 4,743,241 A 5/1988 Igaue et al.
5,807,368 A 9/1998 Helmer
(Continued)

FOREIGN PATENT DOCUMENTS

CN 102371741 3/2012
DE 432986 8/1926
(Continued)

OTHER PUBLICATIONS

International Search Report for PCT/JP2018/017398, dated Jun. 26, 2018.

*Primary Examiner* — Jeffrey A Vonch
(74) *Attorney, Agent, or Firm* — Andrus Intellectual Property Law

(57) ABSTRACT

A disposable wearable article includes an elastic film stretchable structure in which an elastic film is laminated between a first sheet layer and a second sheet layer. The first sheet layer and the second sheet layer are bonded to each other through holes passing through the elastic film with many bonded portions arranged at intervals. A region having the elastic film stretchable structure includes a stretchable region that elastically stretches and contracts together with the elastic film. The stretchable region includes a plurality of elastic films disposed so as to have an overlapping portion. The number of laminated layers of the elastic film in a region located in an intermediate portion of the stretchable region in an orthogonal direction (XD) orthogonal to a stretchable direction (ED) is different from that in each of second regions adjacent to both sides of the first region.

10 Claims, 23 Drawing Sheets

(51) Int. Cl.
| | |
|---|---|
| *B32B 7/05* | (2019.01) |
| *B32B 25/10* | (2006.01) |
| *B32B 27/12* | (2006.01) |
| *A61F 13/49* | (2006.01) |
| *A61F 13/496* | (2006.01) |
| *B32B 5/02* | (2006.01) |
| *B32B 3/26* | (2006.01) |
| *B32B 7/022* | (2019.01) |
| *A61F 13/51* | (2006.01) |
| *A41B 9/00* | (2006.01) |
| *B29C 65/08* | (2006.01) |
| *B29C 65/00* | (2006.01) |
| *B29K 701/12* | (2006.01) |
| *B29L 31/48* | (2006.01) |
| *B32B 3/18* | (2006.01) |
| *B32B 5/14* | (2006.01) |
| *B32B 37/00* | (2006.01) |
| *A61F 13/15* | (2006.01) |

(52) U.S. Cl.
CPC ........ *A61F 13/49019* (2013.01); *A61F 13/51* (2013.01); *B32B 3/266* (2013.01); *B32B 5/022* (2013.01); *B32B 5/24* (2013.01); *B32B 7/022* (2019.01); *B32B 7/05* (2019.01); *B32B 27/12* (2013.01); *A41B 9/001* (2013.01); *A61F 2013/15195* (2013.01); *A61F 2013/49022* (2013.01); *A61F 2013/49033* (2013.01); *A61F 2013/49036* (2013.01); *B29C 65/086* (2013.01); *B29C 66/1122* (2013.01); *B29C 66/344* (2013.01); *B29C 66/41* (2013.01); *B29C 66/7294* (2013.01); *B29K 2701/12* (2013.01); *B29K 2995/0046* (2013.01); *B29L 2031/4878* (2013.01); *B32B 3/18* (2013.01); *B32B 5/145* (2013.01); *B32B 25/10* (2013.01); *B32B 37/0084* (2013.01); *B32B 2250/03* (2013.01); *B32B 2250/40* (2013.01); *B32B 2250/44* (2013.01); *B32B 2274/00* (2013.01); *B32B 2307/51* (2013.01); *B32B 2555/02* (2013.01); *Y10T 428/183* (2015.01); *Y10T 428/19* (2015.01); *Y10T 428/24331* (2015.01); *Y10T 428/24347* (2015.01); *Y10T 428/24826* (2015.01); *Y10T 428/24942* (2015.01); *Y10T 442/659* (2015.04); *Y10T 442/671* (2015.04); *Y10T 442/674* (2015.04); *Y10T 442/678* (2015.04)

(56) References Cited

U.S. PATENT DOCUMENTS

| | | | |
|---|---|---|---|
| 5,846,232 | A | 12/1998 | Serbiak et al. |
| 5,851,935 | A | 12/1998 | Srinivasan et al. |
| 5,899,896 | A | 5/1999 | Surprise et al. |
| 5,931,827 | A | 8/1999 | Buell et al. |
| 6,069,097 | A | 5/2000 | Suzuki et al. |
| 6,245,401 | B1 * | 6/2001 | Ying .................. B32B 5/14 428/218 |
| 6,255,236 | B1 | 7/2001 | Cree et al. |
| 6,610,390 | B1 | 8/2003 | Kauschke et al. |
| 6,682,514 | B1 | 1/2004 | Brunner |
| 2002/0007164 | A1 | 1/2002 | Boggs et al. |
| 2002/0016122 | A1 | 2/2002 | Curro et al. |
| 2002/0023711 | A1 | 2/2002 | Tange |
| 2002/0086602 | A1 | 7/2002 | Friderich et al. |
| 2003/0004481 | A1 | 1/2003 | Matsuoka et al. |
| 2003/0109843 | A1 | 6/2003 | Bernadette |
| 2003/0136497 | A1 | 7/2003 | Hamulski et al. |
| 2004/0044323 | A1 | 3/2004 | Roessler et al. |
| 2005/0215972 | A1 | 9/2005 | Roe et al. |
| 2006/0057924 | A1 | 3/2006 | Cheng et al. |
| 2007/0048497 | A1 | 3/2007 | Zhou et al. |
| 2007/0143972 | A1 | 6/2007 | Kline et al. |
| 2007/0254545 | A1 | 11/2007 | Martin |
| 2008/0051748 | A1 | 2/2008 | Black et al. |
| 2008/0070007 | A1 | 3/2008 | Vincent et al. |
| 2008/0095978 | A1 | 4/2008 | Siqueira et al. |
| 2009/0149827 | A1 | 6/2009 | Mlinar et al. |
| 2009/0191779 | A1 | 7/2009 | Cree et al. |
| 2010/0051170 | A1 | 3/2010 | Nakakado |
| 2010/0163161 | A1 | 7/2010 | Gilgenbach et al. |
| 2010/0168705 | A1 | 7/2010 | Stabelfeldt et al. |
| 2010/0262102 | A1 | 10/2010 | Turner et al. |
| 2010/0285286 | A1 | 11/2010 | Middlesworth |
| 2011/0160691 | A1 | 6/2011 | Ng et al. |
| 2012/0168063 | A1 | 7/2012 | Beuther et al. |
| 2012/0172826 | A1 | 7/2012 | Ng et al. |
| 2012/0302985 | A1 | 11/2012 | Mukai et al. |
| 2013/0079743 | A1 | 3/2013 | Mukai et al. |
| 2013/0138072 | A1 | 5/2013 | Morimoto et al. |
| 2013/0310785 | A1 | 11/2013 | Wade et al. |
| 2014/0093703 | A1 | 4/2014 | Hanschen et al. |
| 2014/0130956 | A1 | 5/2014 | Floberg et al. |
| 2015/0148768 | A1 | 5/2015 | Fukasawa et al. |
| 2015/0164708 | A1 | 6/2015 | Hashimoto et al. |
| 2015/0202095 | A1 | 7/2015 | Kawakami et al. |
| 2015/0297422 | A1 | 10/2015 | Nelson |
| 2017/0087029 | A1 | 3/2017 | Nelson et al. |
| 2017/0182695 | A1 * | 6/2017 | Hanschen ................. B32B 7/12 |
| 2017/0239105 | A1 | 8/2017 | Matsumura |
| 2017/0319399 | A1 | 11/2017 | Desai et al. |
| 2017/0326832 | A1 | 11/2017 | Palzewicz et al. |
| 2017/0348158 | A1 | 12/2017 | You et al. |
| 2017/0362756 | A1 | 12/2017 | Moinard et al. |
| 2018/0008481 | A1 | 1/2018 | Takahashi et al. |
| 2018/0014979 | A1 | 1/2018 | Fujita |
| 2018/0014984 | A1 | 1/2018 | Sakai |
| 2018/0015709 | A1 | 1/2018 | Takeuchi |
| 2018/0028371 | A1 | 2/2018 | Takaishi |
| 2018/0078429 | A1 | 3/2018 | Matsumura |
| 2018/0168874 | A1 | 6/2018 | Lavon et al. |
| 2018/0243145 | A1 | 8/2018 | Wright et al. |
| 2018/0333313 | A1 | 11/2018 | Lavon et al. |
| 2018/0333314 | A1 | 11/2018 | Lavon et al. |
| 2019/0133846 | A1 | 5/2019 | Shirai et al. |
| 2019/0321240 | A1 | 10/2019 | Sakaguchi et al. |
| 2020/0163391 | A1 | 5/2020 | Morishita et al. |

FOREIGN PATENT DOCUMENTS

| | | |
|---|---|---|
| EP | 685586 | 12/1995 |
| JP | 10029259 | 2/1998 |
| JP | 2004-532758 | 10/2004 |
| JP | 4987967 | 8/2012 |
| JP | 5292586 | 9/2013 |
| JP | 5918876 | 5/2016 |
| JP | 2016-189824 | 11/2016 |
| JP | 2016-190031 | 11/2016 |
| JP | 2017-023777 | 2/2017 |
| JP | 2017-064224 | 4/2017 |
| WO | 2008065953 | 6/2008 |
| WO | 2012036599 | 3/2012 |
| WO | 2016052416 | 4/2016 |

* cited by examiner

[FIG.1]
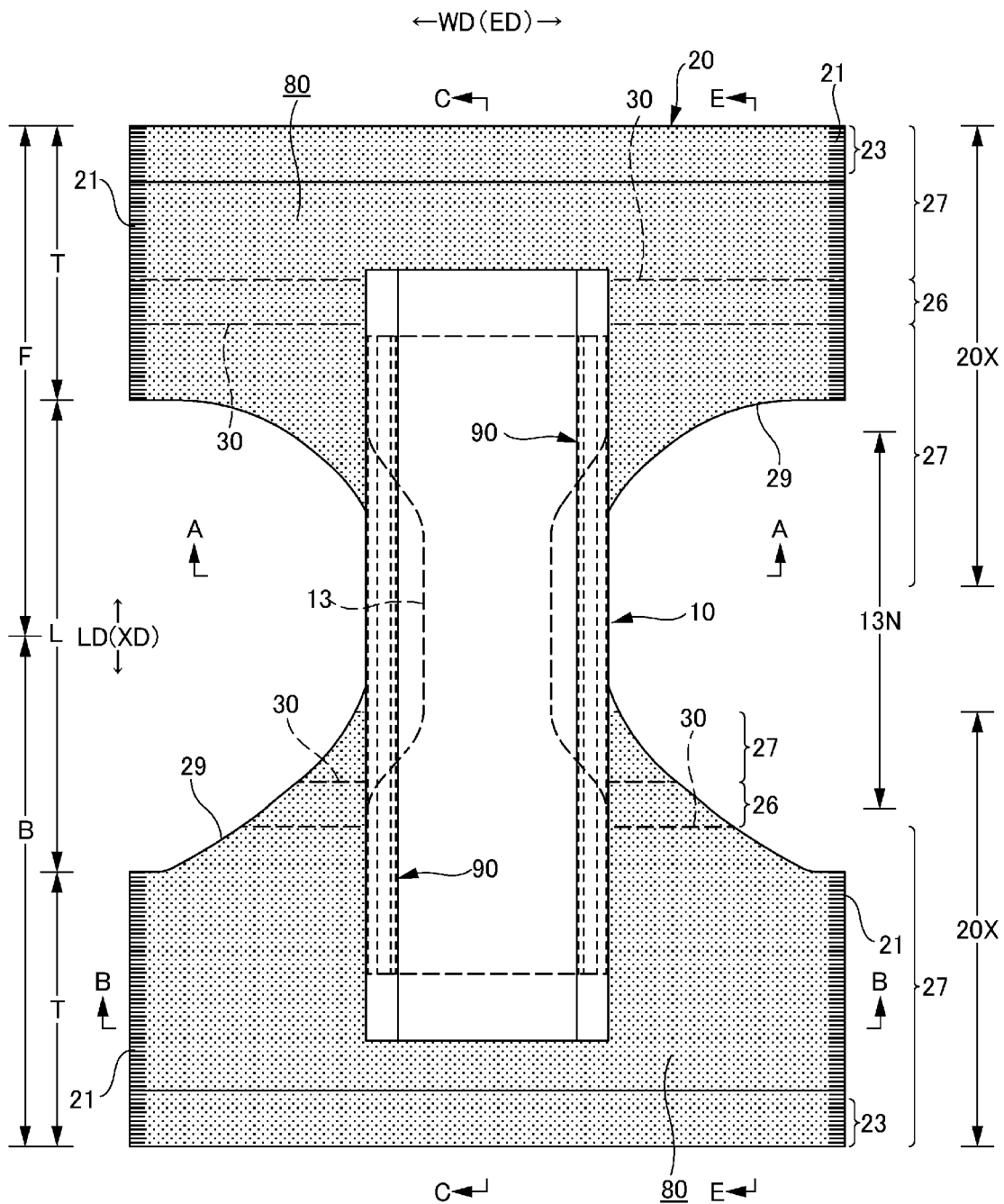

[FIG.2]
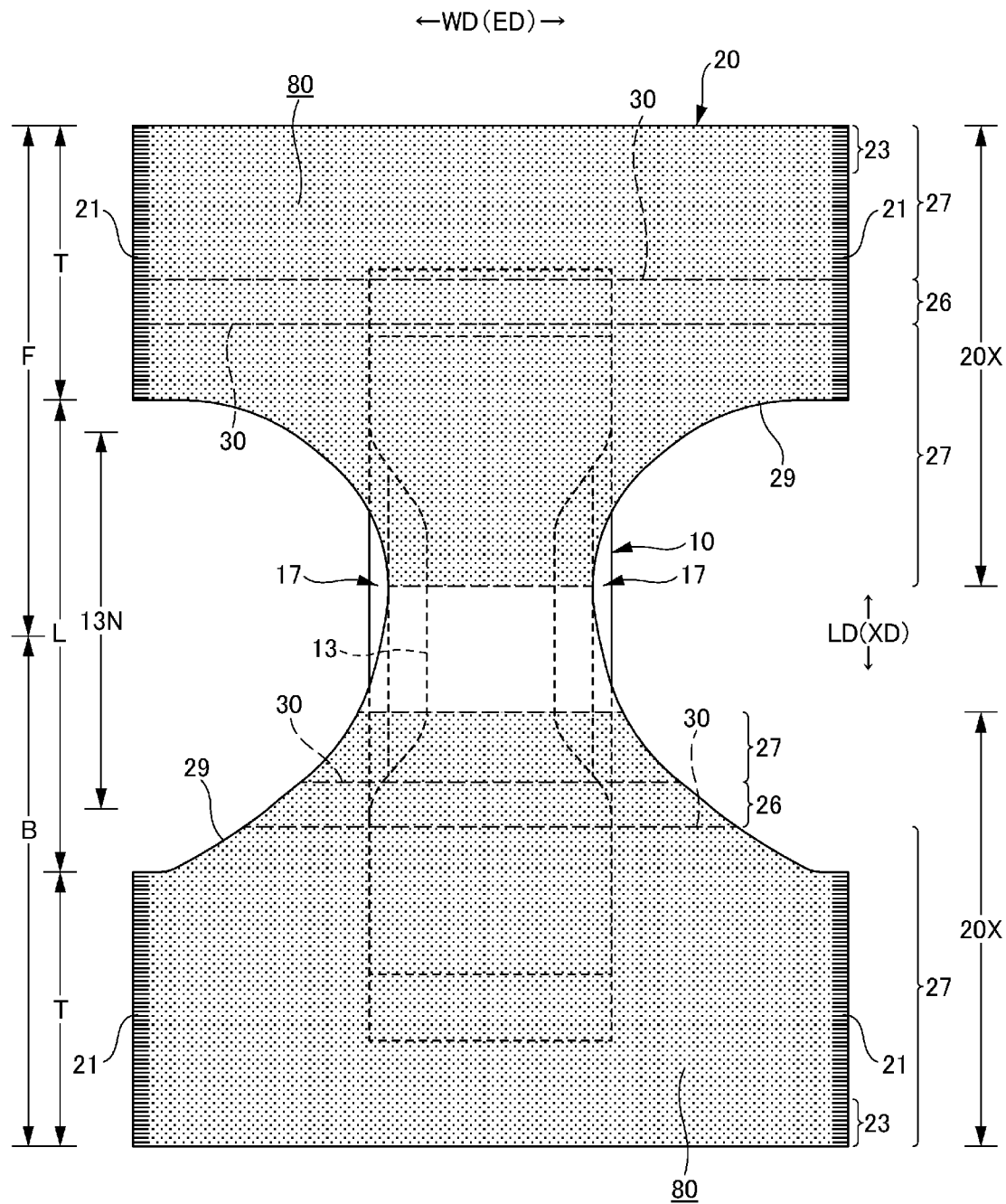

[FIG.3]
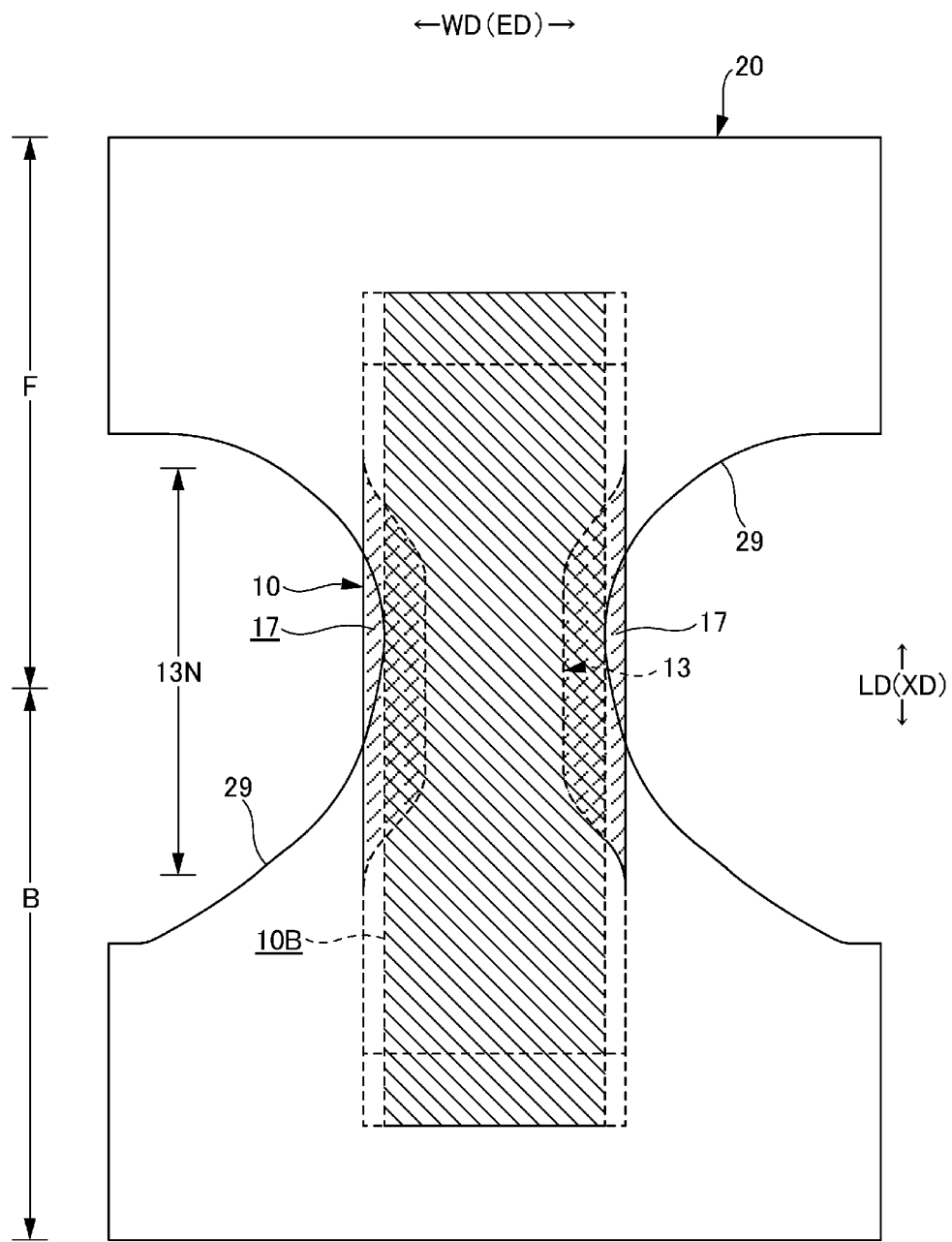

[FIG.5]
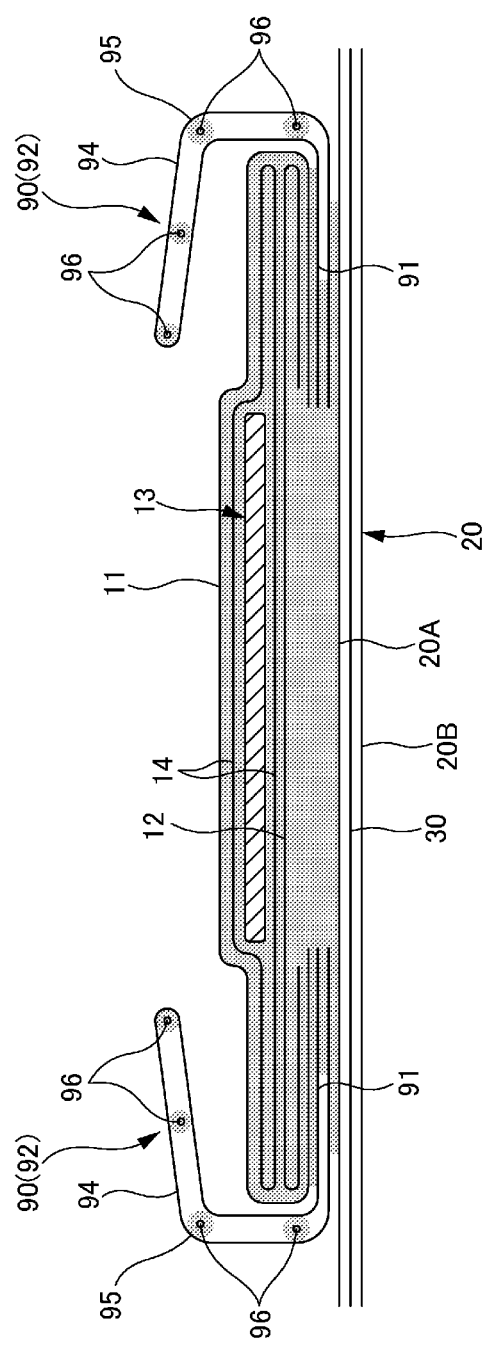

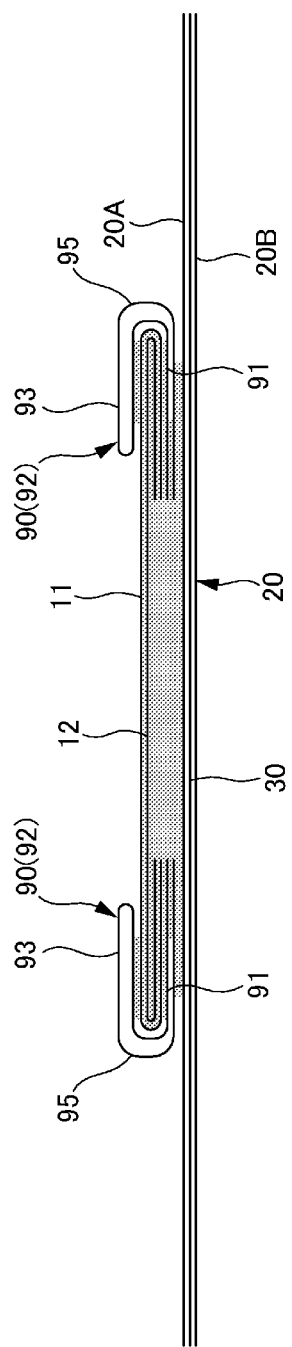
[FIG.6]

[FIG.12]
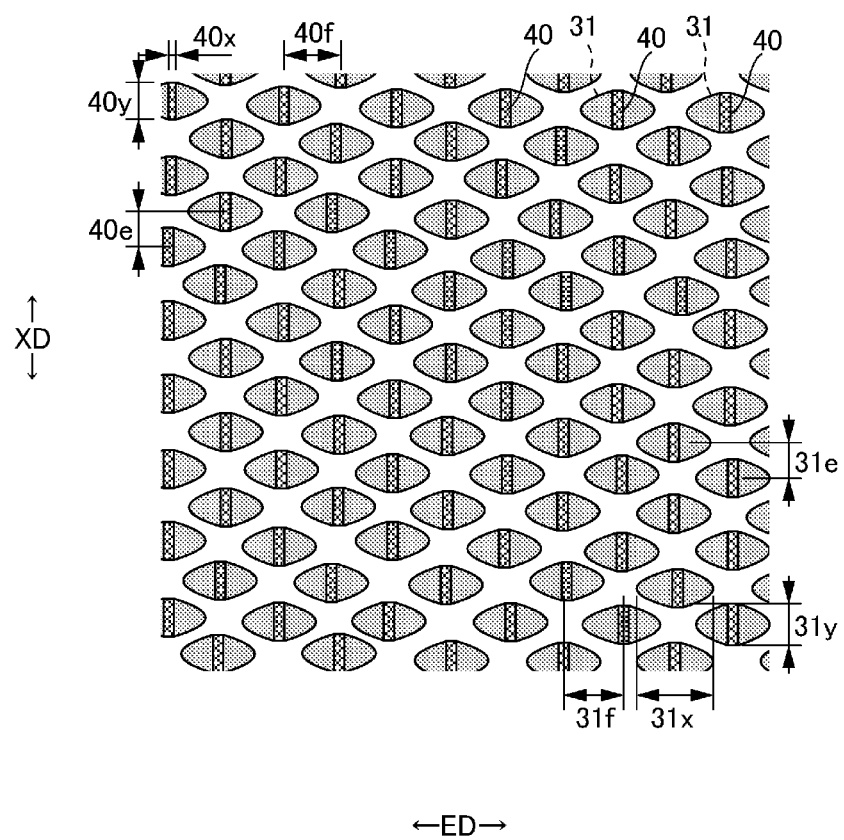

[FIG.14]
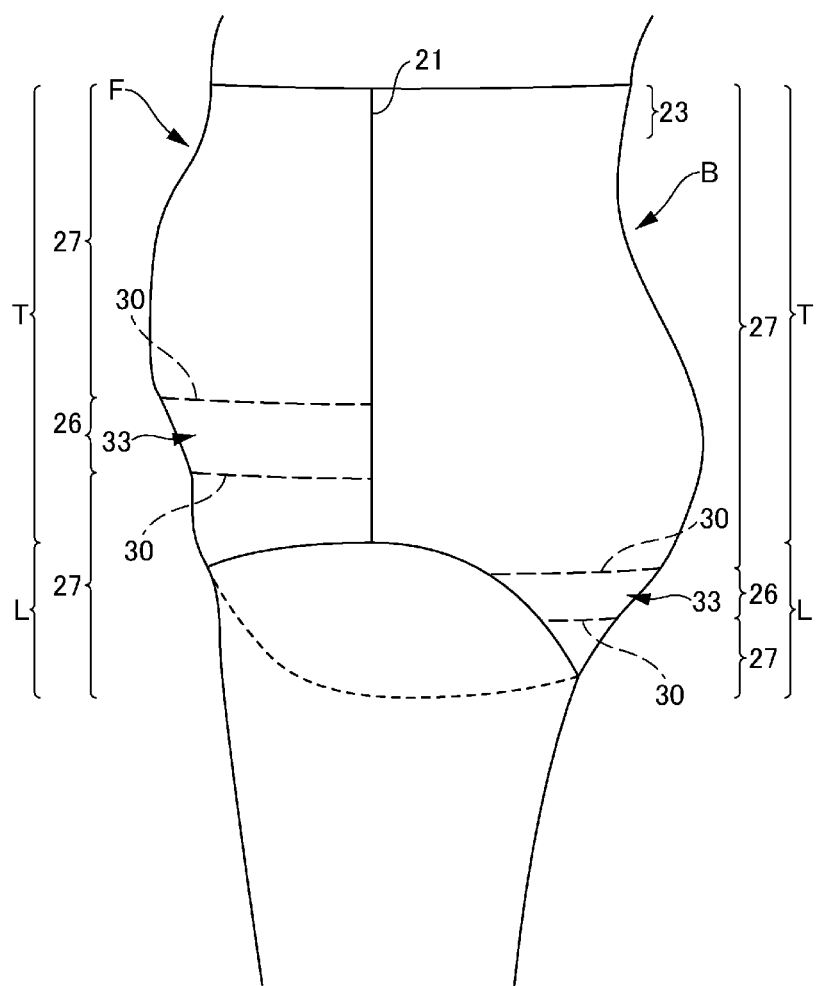

[FIG.15]
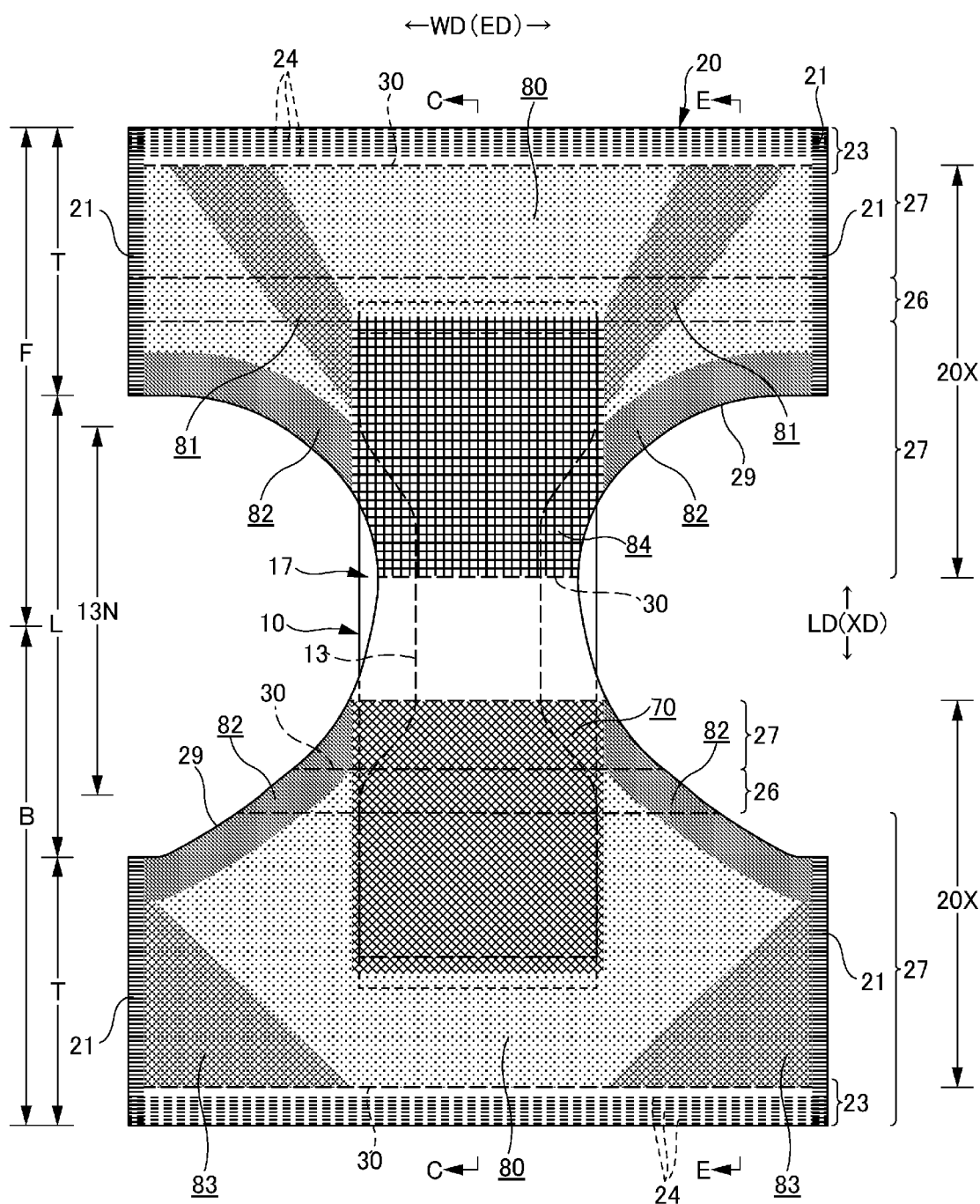

[FIG.21]
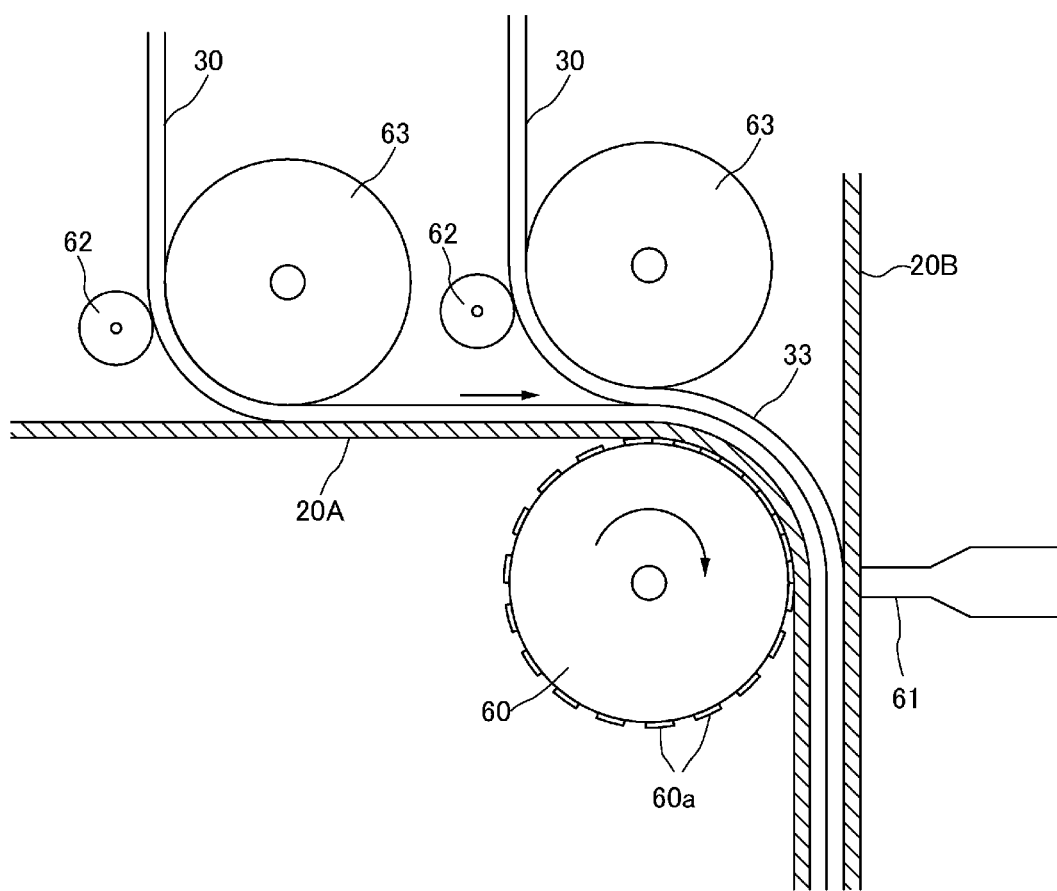

[FIG.22]
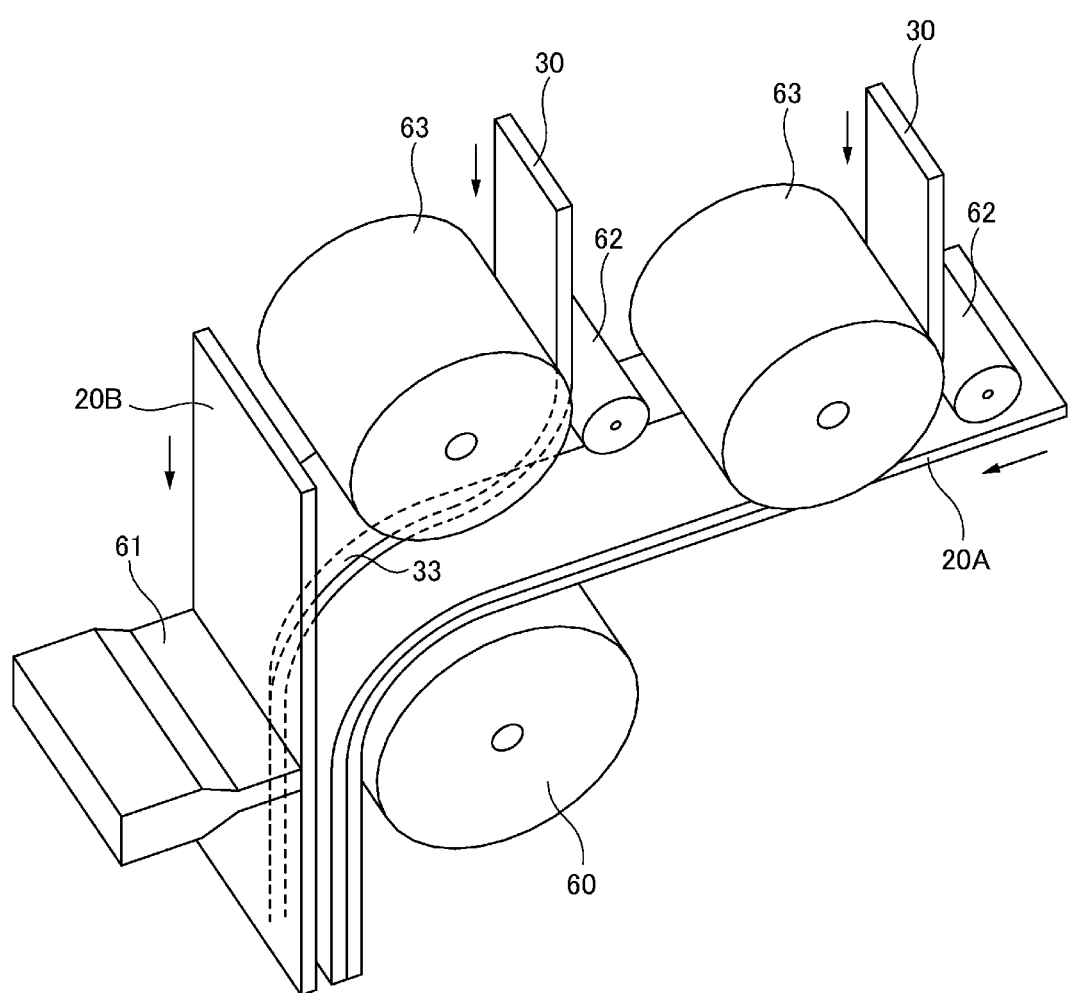

FIG. 23a
FIG. 23b
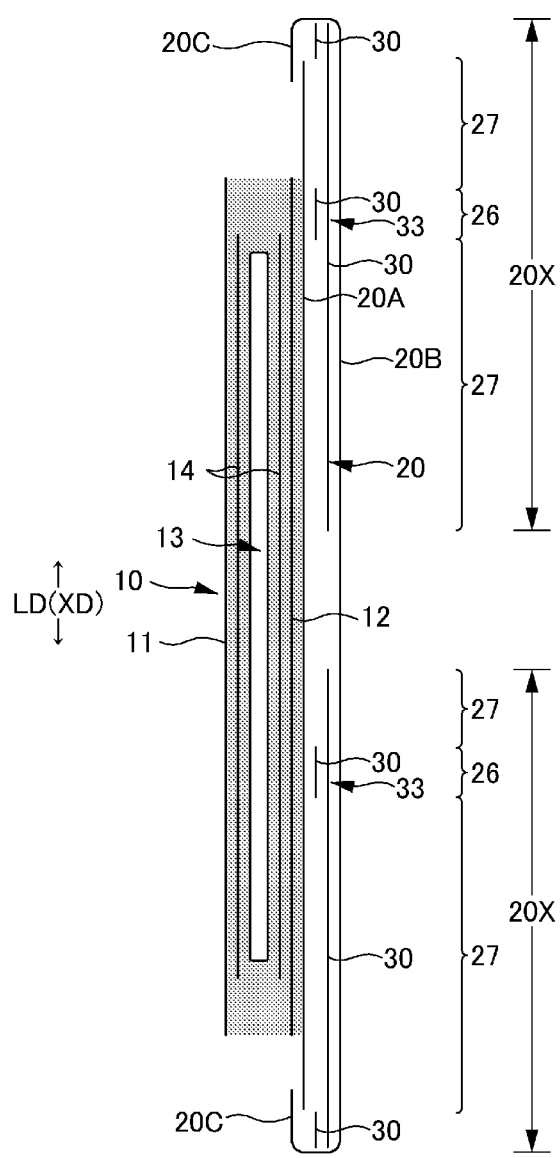
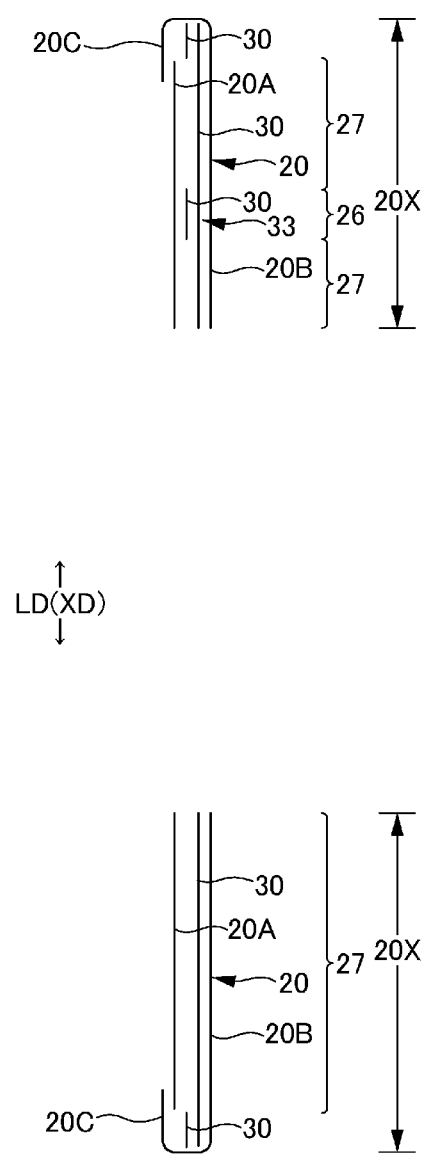

DISPOSABLE WEARABLE ARTICLE

CROSS-REFERENCE TO RELATED APPLICATIONS

The present application is a continuation of U.S. patent application Ser. No. 16/607,248, filed Oct. 22, 2022, which '248 application is the U.S. national stage of International Application No. PCT/JP2018/017398, filed May 1, 2018, which international application was published on Jan. 24, 2019, as International Publication WO 2019/017037 in the Japanese language. The International Application claims priority of Japanese Patent Application No. 2017-140223, filed Jul. 19, 2017. All of which applications are incorporated herein by reference, in entirety.

TECHNICAL FIELD

The present invention relates to a disposable wearable article having an elastic film stretchable structure in which an elastic film is sandwiched between sheet layers.

BACKGROUND ART

In a disposable wearable article such as a disposable diaper or a sanitary napkin, in order to improve fitting to a body surface, elasticity is generally imparted to an appropriate place such as portions around legs or a lower torso. As a technique for imparting elasticity, conventionally, a technique for disposing and fixing many elongated elastically stretchable members such as rubber threads in a state in which the elongated elastically stretchable members are stretched in a longitudinal direction has been widely adopted. However, as a technique having excellent surface fitting, a technique for attaching an elastic film in a state where the elastic film is stretched in an elasticity imparting direction has also been proposed. (For example, see Patent Literatures 1 to 3).

A stretchable structure in which this elastic film is sandwiched between sheet layers (hereinafter also referred to as an elastic film stretchable structure) is obtained by laminating an elastic film between a first sheet layer in which a stretchable region is formed of a nonwoven fabric or the like and a second sheet layer formed of a nonwoven fabric or the like, and bonding the first sheet layer and the second sheet layer to each other through through-holes formed in the elastic film or via the elastic film with many bonded portions arranged at intervals in a stretchable direction and a direction orthogonal thereto in a state where the elastic film is stretched in the stretchable direction. In the stretchable region having such an elastic film stretchable structure, in a natural length state, as the elastic film contracts between the bonded portions, an interval between the bonded portions becomes narrower, and contraction wrinkles extending in a direction crossing the stretchable direction are formed between the bonded portions in the first sheet layer and the second sheet layer. On the contrary, at the time of stretch, as the elastic film stretches between the bonded portions, an interval between the bonded portions and contraction wrinkles in the first sheet layer and the second sheet layer become wider, and elastic stretch is possible until the first sheet layer and the second sheet layer are fully unfolded. This elastic film stretchable structure has an advantage that the through-holes of the elastic film contribute to improvement of air permeability as well as excellent surface fitting.

A disposable wearable article is required to have different fittings depending on a site. Therefore, an intermediate portion of a stretchable region in a direction orthogonal to a stretchable direction desirably has a contraction force at the time of stretch (hereinafter simply referred to as contraction force) different from a contraction force in both sides of the intermediate portion. In this regard, the elastic film stretchable structure can also change a contraction force at the time of stretch in a direction orthogonal to a stretchable direction depending on the area ratio or pattern of bonded portions.

However, only by selecting the area ratio and pattern of the bonded portions, only the contraction force can be reduced, and a contraction ratio also changes. Therefore, this affects an appearance in a natural length state.

Meanwhile, as described in Patent Literatures 2 and 3, a contraction force can be changed depending on a site, for example, a stretchable region due to an elastic film is disposed separately from a stretchable region due to a rubber thread to make a contraction force at a waist portion stronger than that on a crotch side. However, a contraction force does not change within a stretchable region of an elastic film stretchable structure.

The present applicant has proposed an elastic film stretchable structure having a stretchable region in which a stretch rate changes continuously (see Patent Literature 4), and an elastic film stretchable structure in which an elastic film, a first sheet layer, and a second sheet layer are folded back at an edge of an opening, and the edge portion of the opening is tightened more firmly (see Patent Literature 5).

However, in the elastic film stretchable structure described in Patent Literature 4, a contraction force changes continuously, and cannot be changed discontinuously. Even if a contraction force is changed in a direction orthogonal to a stretchable direction, it is difficult to increase a width of the change.

The elastic film stretchable structure described in Patent Literature 5 is based on an assumption that the elastic film, the first sheet layer, and the second sheet layer are folded back. Therefore, an intermediate portion of a stretchable region in a direction orthogonal to a stretchable direction cannot be tightened more firmly than both sides of the intermediate portion.

CITATION LIST

Patent Literature

Patent Literature 1: JP 2004-532758 A
Patent Literature 2: JP 4987967 B2
Patent Literature 3: JP 5292586 B2
Patent Literature 4: JP 2016-189824 A
Patent Literature 5: JP 2016-190031 A

SUMMARY OF INVENTION

Technical Problem

A main object of the present invention is to provide an elastic film stretchable structure in which an intermediate region of a stretchable region in a direction orthogonal to a stretchable direction has a different contraction force from each of adjacent regions adjacent to both sides of the intermediate region.

Solution to Problem

Various aspects that have solved the above problem are as follows.

<First Aspect>

A disposable wearable article having an elastic film stretchable structure in which an elastic film is laminated between a first sheet layer and a second sheet layer, and the first sheet layer and the second sheet layer are bonded to each other through holes passing through the elastic film or via the elastic film with many bonded portions arranged at intervals, a region having the elastic film stretchable structure including a stretchable region that elastically stretches and contracts together with the elastic film, in which the stretchable region includes a plurality of elastic films disposed so as to have an overlapping portion, and the number of laminated layers of the elastic film in a first region located in an intermediate portion of the stretchable region in an orthogonal direction orthogonal to a stretchable direction is different from that in each of second regions adjacent to both sides of the first region.

(Action and Effect)

In the present aspect, the number of laminated layers of the elastic film in the first region located in an intermediate portion of the stretchable region in an orthogonal direction orthogonal to a stretchable direction is different from that in each of the second regions adjacent to both sides of the first region. Therefore, regardless of a change in the pattern of the bonded portions or the stretch rate of the elastic film, a contraction force at the time of stretch can be made different. That is, if the pattern of the bonded portions and the stretch rate of the elastic film are the same between the first region and the second region, a contraction force in a region with a large number of laminated layers is relatively stronger, and a contraction force in a region with a small number of laminated layers is relatively weaker. In addition, unlike a conventional form in which the number of laminated layers is increased by folding, there is no limitation on the number or arrangement of portions with a large number of laminated layers.

<Second Aspect>

The disposable wearable article according to the first aspect, including: a first elastic film extending from one of the second regions to the first region; and a second elastic film extending from the other second region to the first region as the elastic film, in which the one of the second regions includes only the first elastic film as the elastic film, the other second region includes only the second elastic film as the elastic film, and the first region includes the first elastic film and the second elastic film as the elastic film.

(Action and Effect)

The number of elastic films, the number of laminated layers thereof, and arrangement thereof are not particularly limited. However, if the number of laminated layers of the elastic film is large, manufacture may be difficult, for example, it may be difficult to form bonded portions. Therefore, a simple structure as in the present aspect is preferable.

<Third Aspect>

The disposable wearable article according to the second aspect, in which a stretch stress at the time of 4-times stretch in the stretchable direction in the first elastic film is different from a stretch stress at the time of 4-times stretch in the stretchable direction in the second elastic film.

(Action and Effect)

As in the present aspect, by using the first elastic film and the second elastic film having different stretch stresses, a contraction force can be made different among the three regions consisting of the one of the second regions, the first region, and the other second region while the simple structure of the second aspect is maintained.

<Fourth Aspect>

The disposable wearable article according to the second or third aspect, in which an elongation at elastic limit of the one of the second regions is different from that of the other second region, and the larger elongation at elastic limit thereof is the same as the elongation at elastic limit of the first region.

(Action and Effect)

When the first sheet layer and the second sheet layer are bonded to each other in manufacture, if the stretch rates of the elastic films are made different from each other, as in the present aspect, the elongation at elastic limit of one of the second regions is different from that of the other second region, and the larger elongation at elastic limit is the same as the elongation at elastic limit of the first region. In the present aspect, when the stretchable region is stretched in the stretchable direction from an initial stage at which both the elastic films are in a natural length state, the stretchable region comes to a wearing stage at which both the elastic films are in a stretched state through an intermediate stage at which one of the elastic films is in a natural length state, and the other elastic film is in a stretched state. Therefore, when the stretchable region is stretched for wearing, the first region initially stretches with the same stretch stress as the second region with a larger elongation at elastic limit, and the stretch stress is the strongest at a wearing stage. Therefore, the article is easily worn, and obtains firm fitting in a wearing state.

<Fifth Aspect>

The disposable wearable article according to any one of the first to fourth aspects, which is an underpants-type disposable wearable article including:

a front-back separated or front-back integrated outer member including a front body lower torso portion, a back body lower torso portion, and an intermediate portion located therebetween; and an inner member attached to the outer member and extending from the front body to the back body via a crotch portion, in which both sides of the outer member in the front body are bonded to both sides of the outer member in the back body to form a side seal portion and to form a waist opening and a pair of left and right leg openings, and at least one of the outer member of the front body and the outer member of the back body has the stretchable region that stretches and contracts in a width direction.

(Action and Effect)

In an underpants-type disposable wearable article, a stretchable region that stretches and contracts in a width direction is generally disposed in an outer member. In consideration of fitting to a bulge of a lower abdomen portion and fitting to a bulge of a gluteal region, in at least one of the outer member of the front body and the outer member of the back body, the first region of the stretchable region in a direction orthogonal to the stretchable direction preferably has a contraction force different from each of the second regions adjacent to both sides of the first region.

<Sixth Aspect>

The disposable wearable article according to any one of the first to fifth aspects, in which the outer member of the front body has the stretchable region in the lower torso portion, and the outer member of the back body has the stretchable region from the lower torso portion to the intermediate portion, each of the stretchable regions includes a first elastic film extending from one of the second regions to the first region, and a second elastic film extending from the other second region to the first region as the elastic film, the one of the second regions includes only the first elastic film as the elastic film, the other second region includes only the second elastic film as the elastic film, the first region includes the first elastic film and the second elastic film as the elastic film, the outer member of the front body has the first region in the lower torso portion, and the outer member of the back body has the first region in the intermediate portion.

(Action and Effect)

By disposing the first region in which the first elastic film and the second elastic film overlap with each other and the second region including only the first elastic film or only the second elastic film asymmetrically in a front-back direction as in the present aspect, favorable fitting to a lower abdomen portion and a lower gluteal region (gluteal groove) where a gap is easily generated is achieved. In addition, the position of the first region of the front body is different from the position of the first region of the back body in the side seal portion. Therefore, the number of laminated layers of a material in the side seal portion does not become locally too large. This prevents deterioration of wearing feeling and sealing failure of the side seal portion.

<Seventh Aspect>

The disposable wearable article according to the sixth aspect, in which in the first elastic film and the second elastic film, a stretch stress at the time of 4-times stretch in the stretchable direction in the elastic film on the waist opening side is weaker than that in the elastic film on the opposite side.

(Action and Effect)

As in the present aspect, by using the first elastic film and the second elastic film having different stretch stresses, a portion where a gap is easily generated at the time of wearing can be firmly tightened, and a contraction force of a portion closer to a waist opening than the portion where a gap is easily generated can be minimized to reduce tightening feeling on the waist opening side.

Advantageous Effects of Invention

As described above, the present invention provides, for example, an elastic film stretchable structure in which an intermediate region of a stretchable region in a direction orthogonal to a stretchable direction has a different contraction force from each of adjacent regions adjacent to both sides of the intermediate region advantageously.

BRIEF DESCRIPTION OF DRAWINGS

FIG. 1 is a plan view (internal surface side) of an underpants-type disposable diaper in an unfolded state.

FIG. 2 is a plan view (external surface side) of an underpants-type disposable diaper in an unfolded state.

FIG. 3 is a plan view illustrating only a main part of an underpants-type disposable diaper in an unfolded state.

FIG. 5 is a cross-sectional view taken along line A-A in FIG. 1.

FIG. 6 is a cross-sectional view taken along line B-B in FIG. 1.

FIG. 12 is a trace view of a photograph of a non-stretchable region of a sample.

FIG. 14 is a left side view schematically illustrating a wearing state.

FIG. 15 is a plan view (external surface side) of an underpants-type disposable diaper in an unfolded state.

FIG. 21 is a schematic view of an ultrasonic sealing device.

FIG. 22 is a schematic perspective view of an ultrasonic sealing device.

FIG. 23(a) is a cross-sectional view taken along line C-C in FIG. 1, and FIG. 23(b) is a cross-sectional view taken along line E-E in FIG. 1.

DESCRIPTION OF EMBODIMENTS

Figure 4A:
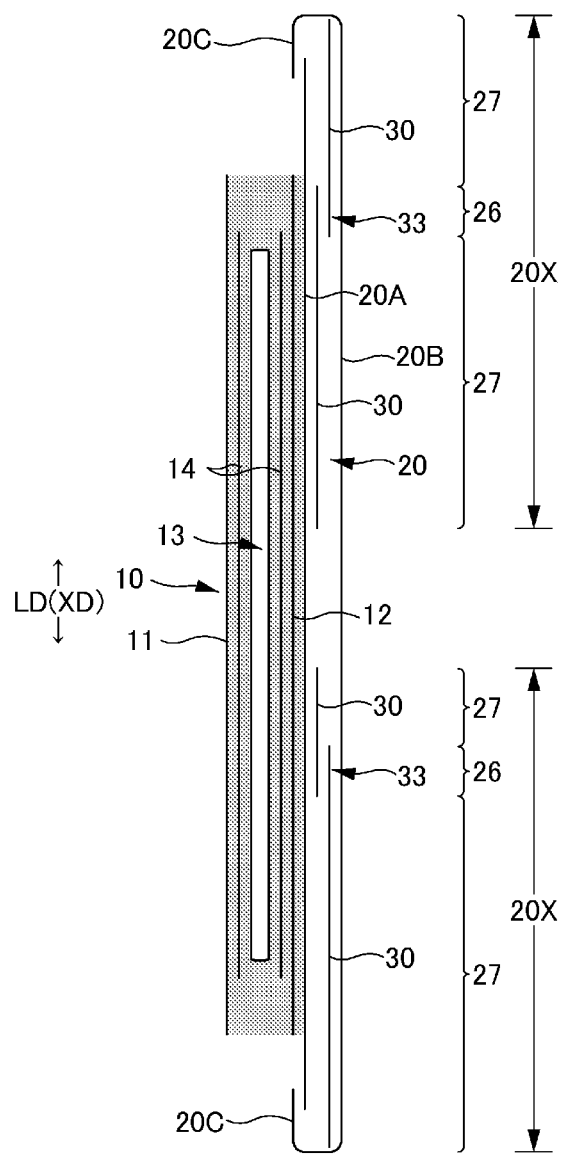
FIG. 4(a) is a cross-sectional view taken along line C-C in FIG. 1.

Hereinafter, the present invention will be described in detail with reference to the attached drawings. Note that a dotted pattern portion in a cross-sectional view illustrates a bonding means such as a hot melt adhesive.

FIGS. 1 to 6 illustrate an example of an underpants-type disposable diaper. This underpants-type disposable diaper (hereinafter also simply referred to as a diaper) includes an outer member 20 forming a front body F and a back body B, and an inner member 10 fixed to and integrated with an inner surface of the outer member 20. The inner member 10 is formed by interposing an absorber 13 between a liquid pervious top sheet 11 and a liquid impervious sheet 12. In manufacture, a back surface of the inner member 10 is bonded to an inner surface (upper surface) of the outer member 20 by a bonding means such as a hot melt adhesive. Thereafter, the inner member 10 and the outer member 20 are folded at the center in a front-back direction LD (longitudinal direction) that is a boundary between the front body F and the back body B. Both side portions thereof are bonded to each other by heat welding, a hot melt adhesive, or the like to form a side seal portion 21, thus forming an underpants-type disposable diaper with a waist opening and a pair of left and right leg openings.

(Structure Example of Inner Member)

Figure 4B:
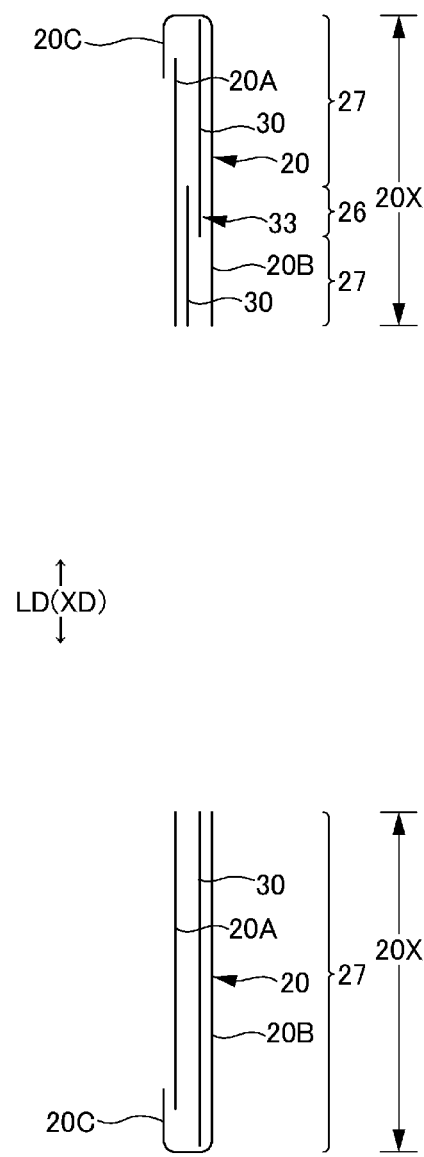
FIG. 4(b) is a cross-sectional view taken along line E-E in FIG. 1.

As illustrated in FIGS. 4 to 6, the inner member 10 has a structure in which the absorber 13 is interposed between the top sheet 11 and the liquid impervious sheet 12 made of polyethylene or the like, and absorbs and holds an excretory liquid that has passed through the top sheet 11. The planar shape of the inner member 10 is not particularly limited, but is generally rectangular as illustrated in FIG. 1.

As the top sheet 11 covering a front surface side (skin side) of the absorber 13, a porous or non-porous nonwoven fabric or a porous plastic sheet is preferably used. Examples of a material fiber constituting the nonwoven fabric include a synthetic fiber such as a polyolefin-based fiber including polyethylene and polypropylene, a polyester-based fiber, or a polyamide-based fiber, a regenerated fiber such as rayon or cupra, and a natural fiber such as cotton. A nonwoven fabric obtained by an appropriate processing method such as a spunlace method, a spunbond method, a thermal bond method, a melt blown method, or a needle punch method can be used. Among these processing methods, the spunlace method is excellent from viewpoints of high flexibility and drapeability, and the thermal bond method is excellent from viewpoints of bulkiness and softness. When many through-holes are formed in the top sheet 11, urine or the like is quickly absorbed, and an excellent dry touch property is achieved. The top sheet 11 is wound around a side edge portion of the absorber 13 and extends to a back surface side of the absorber 13.

As the liquid impervious sheet 12 covering a back surface side (non-skin side) of the absorber 13, a liquid impervious plastic sheet such as polyethylene or polypropylene is used. However, in recent years, a moisture permeable sheet is preferably used from a viewpoint of preventing stuffiness. The water shielding and moisture permeable sheet is a microporous sheet obtained by melt kneading an inorganic filler in an olefin resin such as polyethylene or polypropylene to form a sheet, and then stretching the sheet in a monoaxial or biaxial direction. In the illustrated example, the liquid impervious sheet 12 is folded back to a back surface side on both sides of the absorber 13 in the width direction together with the top sheet 11, but the liquid impervious sheet 12 is not limited thereto.

As the absorber 13, a known absorber, for example, an absorber obtained by mixing or fixing a super absorbent polymer as necessary on the basis of a pulp fiber stack, an assembly of filaments such as cellulose acetate, or a nonwoven fabric can be used. The absorber 13 can be wrapped by a wrapping sheet 14 having liquid perviousness and a liquid holding property, such as crepe paper, as necessary, for holding the shape and a polymer, for example.

The shape of the absorber 13 is formed into a substantially hourglass shape having a narrowing portion 13N narrower than both the front and back sides at a crotch portion. The size of the narrowing portion 13N can be determined appropriately, but the length of the narrowing portion 13N in the front-back direction can be about 20 to 50% of the maximum length of a diaper. The width of the narrowest portion can be about 40 to 60% of the maximum width of the absorber 13. In a case where such a narrowing portion 13N is included, if the planar shape of the inner member 10 is substantially rectangular, in a portion corresponding to the narrowing portion 13N of the absorber 13 in the inner member 10, a non-absorber side portion 17 including no absorber 13 is formed.

Three-dimensional gathers 90 that fit a body surface are formed on both sides of the inner member 10. As illustrated in FIGS. 5 and 6, each of the three-dimensional gathers 90 includes a fixed portion 91 fixed to a side portion of a back surface of the inner member 10, a main unit portion 92 extending from the fixed portion 91 up to a side portion of a surface of the inner member 10 through a side of the inner member 10, a fallen portion 93 formed by fixing front and back end portions of the main unit portion 92 to a side portion of a surface of the inner member 10 (the top sheet 11 in the illustrated embodiment) in a fallen state, and a free portion 94 formed by making a portion between the fallen portions 93 non-fixed. Each of these portions is formed of a gather sheet 95 that is a duplicate sheet obtained by folding back a sheet such as a nonwoven fabric. The gather sheet 95 is attached over the entire front-back direction of the inner member 10. The fallen portion 93 is disposed in front of the non-absorber side portion 17 and behind the non-absorber side portion 17. The free portion 94 extends to both the front and back sides of the non-absorber side portion 17. Between the double gather sheets 95, an elongated elastically stretchable gather member 96 is disposed at a tip of the free portion or the like. As illustrated in FIG. 5, the elastically stretchable gather member 96 is for raising the free portion 94 by an elastic contraction force in a product state.

The three-dimensional gather 90 illustrated in FIGS. 5 and 6 has a form in which the main unit portion 92 is not folded back. However, any known form can be adopted, such as a form in which a root side portion of the main unit portion 92 rises obliquely toward the center in the width direction, and a portion closer to a tip than the intermediate portion rises obliquely outward in the width direction.

As the elastically stretchable gather member 96, a usually used material such as a polystyrene-based rubber, a polyolefin-based rubber, a polyurethane-based rubber, a polyester-based rubber, polyurethane, polyethylene, polystyrene, styrene-butadiene copolymer, silicone, or polyester can be used. In order to make it difficult to see the elastically stretchable gather member 96 from the outside, the elastically stretchable gather member 96 preferably has a fineness of 925 dtex or less, a tension of 150 to 350%, and an interval of 7.0 mm or less. Note that as the elastically stretchable gather member 96, a tape-like member having a certain width can be used in addition to a thread-like member as in the illustrated embodiment.

Similarly to the top sheet 11, as a material fiber constituting the gather sheet 95, preferably, in addition to a synthetic fiber such as a polyolefin-based fiber including polyethylene and polypropylene, a polyester-based fiber, or a polyamide-based fiber, a regenerated fiber such as rayon or cupra, and a natural fiber such as cotton can be used. A nonwoven fabric obtained by an appropriate processing method such as a spunbond method, a thermal bond method, a melt blown method, or a needle punch method can be used. Particularly, a nonwoven fabric having a reduced basis weight and excellent air permeability is preferably used in order to prevent stuffiness. Furthermore, as the gather sheet 95, in order to prevent urine or the like from passing through the gather sheet 95, to prevent rash, and to enhance feeling (dry feeling) to a skin, it is desirable to use a water repellent nonwoven fabric coated with, for example, a silicone-based, paraffin metal-based, or alkylchromic chloride-based water repellent agent.

(Structure Example of Outer Member)

The outer member 20 extends from a side edge of the inner member 10 in the side direction. The outer member 20 may have a side edge located closer to the center in the width direction than a side edge of the inner member 10 at a crotch portion as in the illustrated embodiment, or may be located outward in the width direction. The outer member 20 has lower torso portions T that are front-back direction ranges corresponding to the side seal portions 21, and an intermediate portion L that is a front-back direction range between the lower torso portion T of the front body F and the lower torso portion T of the back body B. The planar shape of the outer member 20 is formed such that each of both side edges 29 of the intermediate portion L in the width direction is curved along a portion around a leg, and has a shape similar to an hourglass as a whole. The outer member 20 may be formed for each of the front body F and the back body B so as to be separated from each other in the front-back direction LD at a crotch portion.

The outer member 20 of the example illustrated in FIGS. 1 to 6 has an elastic film stretchable structure 20X in which a stretchable direction ED is a width direction WD except for an intermediate portion of the intermediate portion L in the front-back direction. More specifically, as illustrated in FIGS. 2 and 4 to 6, the elastic film stretchable structure 20X has the elastic film 30 laminated between the first sheet layer 20A and the second sheet layer 20B, and as illustrated in FIG. 7, the first sheet layer 20A and the second sheet layer 20B are bonded to each other through through-holes 31 passing through the elastic film 30 with many bonded portions 40 arranged at intervals. The first sheet layer 20A and the second sheet layer 20B may be bonded to each other indirectly via the elastic film 30 instead of through the through-holes 31 of the elastic film 30.

Figure 16A:
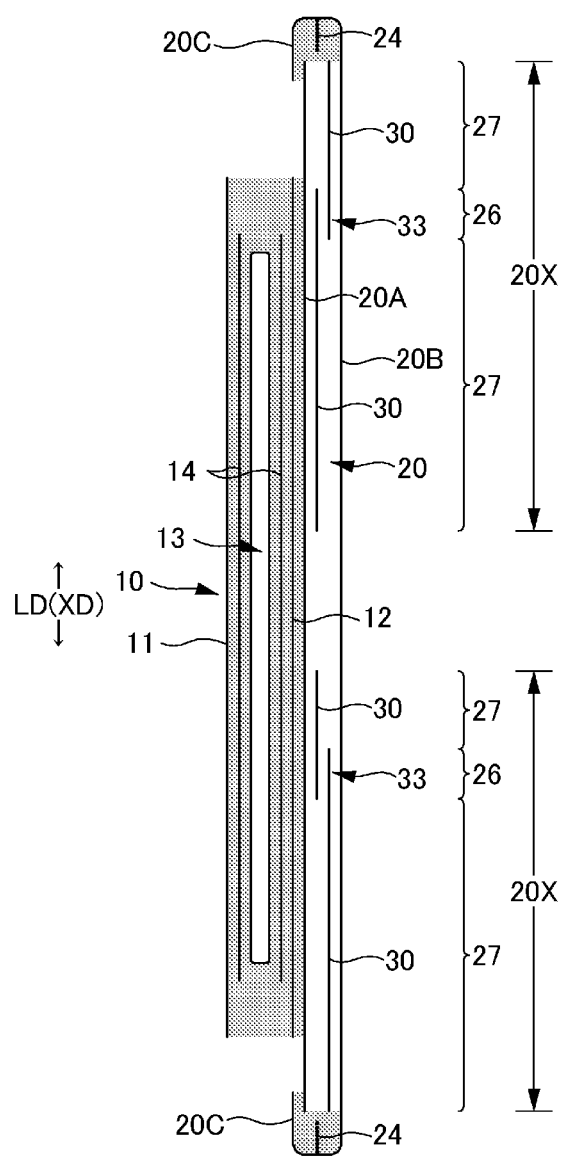
FIG. 16(a) is a cross-sectional view taken along line C-C in FIG. 15.
Figure 16B:
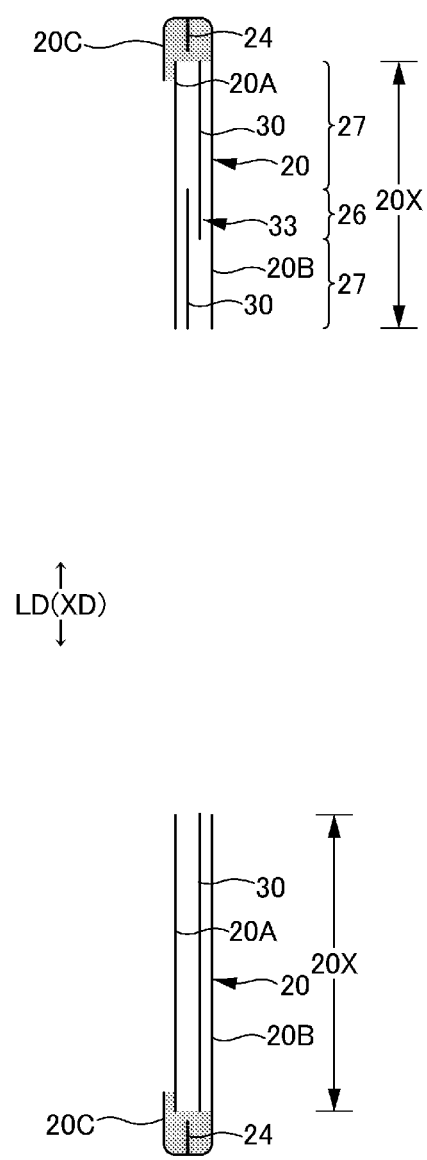
FIG. 16(b) is a cross-sectional view taken along line E-E in FIG. 15.

The form illustrated in FIGS. 1 and 2 is a form in which the elastic film stretchable structure 20X extends up to a waist portion 23. However, if the elastic film stretchable structure 20X is used for the waist portion 23, for example, the waist portion 23 is not sufficiently tightened. As illustrated in FIGS. 15 and 16, the waist portion 23 can have a stretchable structure by a conventional elongated waist portion elastic member 24 as necessary without having the elastic film stretchable structure 20X. However, in the illustrated example, at an edge portion of a leg opening in the outer member 20, an elongated elastically stretchable member extending along the leg opening is not disposed. The waist portion elastic member 24 is an elongated elastic member such as a plurality of rubber threads disposed at intervals in the front-back direction LD, and applies a stretching force so as to tighten a lower torso of a body. The waist portion elastic members 24 are not disposed substantially in a bundle at close intervals, but three or more, preferably five or more waist portion elastic members 24 are disposed at about 3 to 8 mm intervals so as to form a predetermined stretchable zone. The stretch rate of the waist portion elastic member 24 at the time of fixing can be determined appropriately, but can be about 230 to 320% for a normal adult. As the waist portion elastic member 24, a rubber thread is used in the illustrated example, but other elongated stretchable members such as flat rubber may be used. Although not illustrated, a general-purpose form may be adopted in which only the elongated elastically stretchable member such as a rubber thread or flat rubber is disposed without the elastic film stretchable structure 20X disposed on the outer member 20.

Although not illustrated, another form may be, for example, a form in which the intermediate portion L between the lower torso portion T of the front body F and the lower torso portion T of the back body B does not have the elastic film stretchable structure 20X, a form in which the elastic film stretchable structure 20X is continuously disposed in the front-back direction LD from the lower torso portion T of the front body F up to the lower torso portion T of the back body B through the intermediate portion L, or a form in which only either the front body F or the back body B has the elastic film stretchable structure 20X. Appropriate modifications are also possible.

Figure 13A:
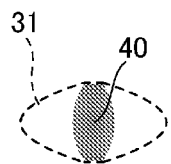
FIGS. 13(a)-13(d) are an enlarged plan views of a main part of a non-stretchable region.
Figure 13B:
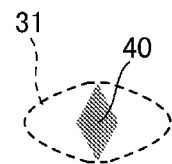
Figure 13C:
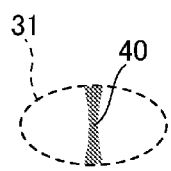

The shape of each of the bonded portions 40 and the through-holes 31 in a natural length state can be determined appropriately, and can be any shape such as a perfect circle (see FIGS. 7 and 8), an ellipse, a polygon such as a triangle, a rectangle (see FIGS. 9 to 12), or a rhombus (see FIG. 13(b)), a convex lens shape (see FIG. 13(a)), a concave lens shape (see FIG. 13(c)), a star shape, or a cloud shape. The size of each of the bonded portions 40 is not particularly limited. However, the maximum length thereof is preferably 0.5 to 3.0 mm, and particularly preferably 0.7 to 1.1 mm. The maximum width 40x thereof is preferably 0.1 to 3.0 mm, and is preferably 0.1 to 1.1 mm particularly in a case of a long shape in an orthogonal direction XD orthogonal to the stretchable direction ED.

The size of each of the bonded portions 40 only needs to be determined appropriately. However, if the size is too large, an influence of the hardness of the bonded portion 40 on feeling increases, and if the size is too small, a bonded area is small and materials cannot sufficiently be bonded to each other. Therefore, in a normal case, the area of each of the bonded portions 40 is preferably about 0.14 to 3.5 mm$^2$. The area of an opening of each of the through-holes 31 only needs to be equal to or larger than the area of the bonded portion 40 because the bonded portion 40 is formed through the through-hole 31. However, the area of an opening of each of the through-holes 31 is preferably about 1 to 1.5 times the area of the bonded portion 40. Note that the area of an opening of the through-hole 31 means a value not in a state of the elastic film 30 alone but in a state of being integrated with the first sheet layer 20A and the second sheet layer 20B and in a natural length state. When the area of an opening of the through-hole 31 is not uniform in the thickness direction, such as when the area of an opening of the through-hole 31 is different between the front and the back of the elastic film 30, the area of an opening of the through-hole 31 means a minimum value.

Figure 20A:
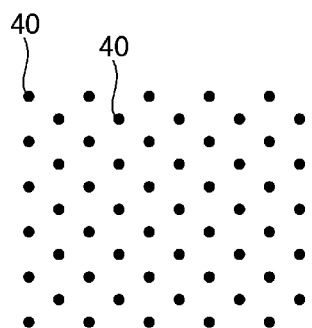
FIGS. 20(a)-20(e) are plan views illustrating various arrangement examples of bonded portions.
Figure 20B:
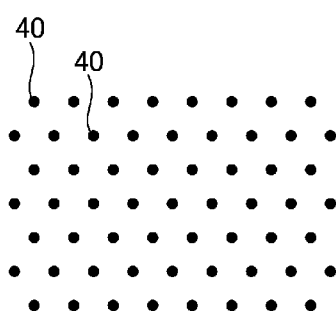
Figure 20C:
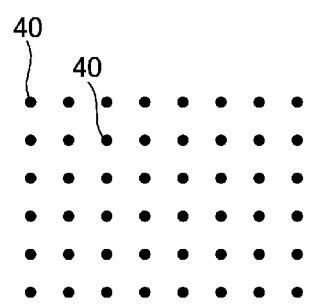
Figure 20D:
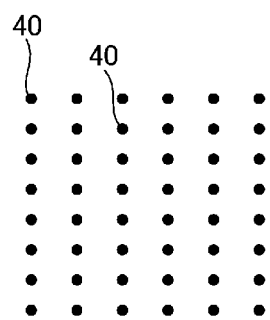
Figure 20E:
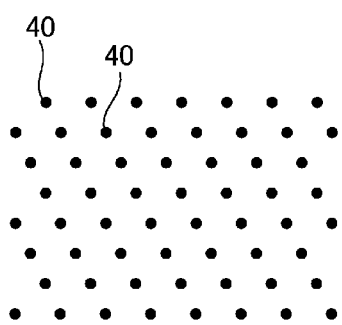

A planar arrangement of the bonded portions 40 and the through-holes 31 can be determined appropriately, but a regularly repeated planar arrangement is preferable. In addition to a regularly repeated planar arrangement such as an oblique lattice shape as illustrated in FIG. 20(a), a hexagonal lattice shape (these are also called a zigzag shape) as illustrated in FIG. 20(b), a square lattice shape as illustrated in FIG. 20(c), a rectangular lattice shape as illustrated in FIG. 20(d), or a parallel lattice (a form in which two groups are disposed such that many groups of parallel diagonal rows intersect each other as illustrated in the drawing) shape as illustrated in FIG. 20(e) (including a form in which these are inclined at an angle of less than 90 degrees with respect to the stretchable direction ED), a form in which a group of the bonded portions 40 (group units may be arranged regularly or irregularly, and may have a pattern shape or a letter shape) is regularly repeated may be adopted.

When the first sheet layer 20A and the second sheet layer 20B in the bonded portion 40 are bonded to each other through the through-holes 31 formed in the elastic film 30, it is desirable that the first sheet layer 20A and the second sheet layer 20B are not bonded to the elastic film 30 except for at least a portion between the first sheet layer 20A and the second sheet layer 20B in the bonded portion 40.

A means for bonding the first sheet layer 20A and the second sheet layer 20B in the bonded portion 40 to each other is not particularly limited. For example, the first sheet layer 20A and the second sheet layer 20B in the bonded portion 40 may be bonded to each other with a hot melt adhesive or by a bonding means by material welding such as heat sealing or ultrasonic sealing.

Figure 17A:
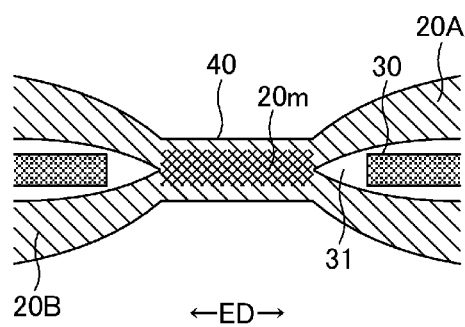
FIGS. 17a-17c are cross-sectional views schematically illustrating a cross-section of a main part of an outer member that has stretched to some extent.
Figure 17B:
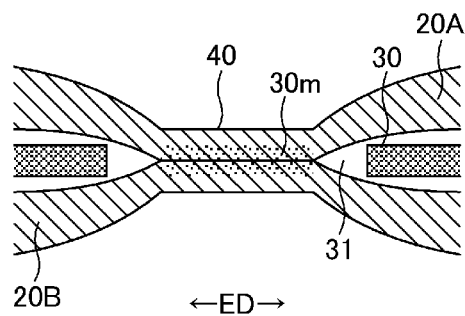
Figure 17C:
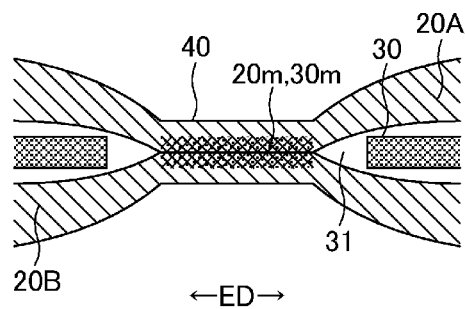
Figure 19A:
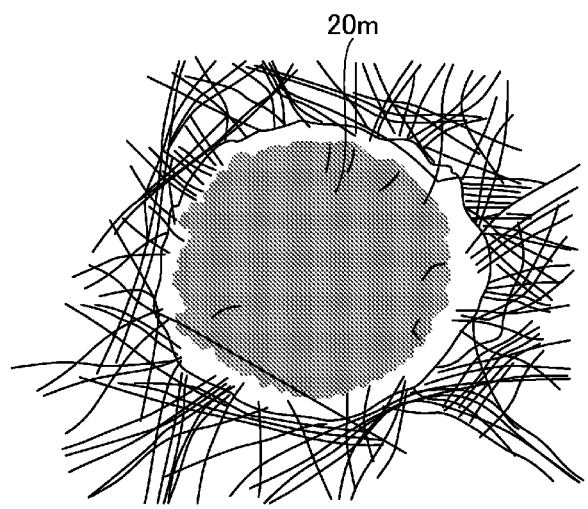
FIG. 19(a) is a trace view of a plane photograph of a bonded portion formed in a first welding form.
Figure 19B:
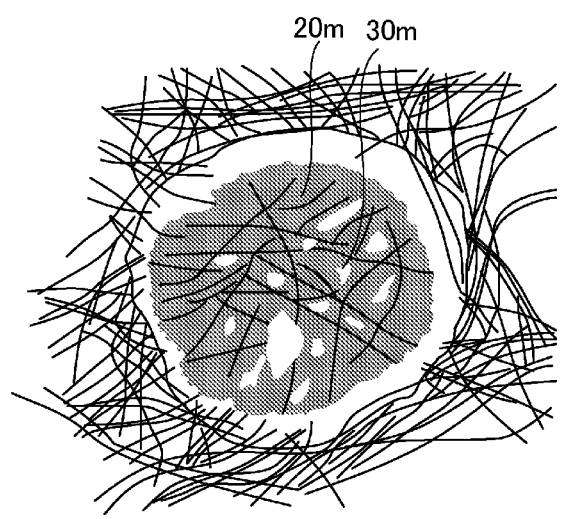
FIG. 19(b) is a trace view of a plane photograph of a bonded portion formed in a third welding form.

When the first sheet layer 20A and the second sheet layer 20B in the bonded portion 40 are bonded to each other through the through-hole 31 of the elastic film 30, a form in which the bonded portion 40 is formed by material welding may be any one of a first welding form in which the first sheet layer 20A and the second sheet layer 20B are bonded to each other only with a molten and solidified material 20m of a most part or a part of at least one of the first sheet layer 20A and the second sheet layer 20B in the bonded portion 40 (see FIG. 17(a)), a second welding form in which the first sheet layer 20A and the second sheet layer 20B are bonded to each other only with a molten and solidified material 30m of the entire part, a most part, or a part of the elastic film 30 in the bonded portion 40 (see FIG. 17(b)), and a third welding form in which both of the first welding form and the second welding form are combined (see FIG. 17(c)), but the second and third welding forms are preferable. Particularly preferably, the first sheet layer 20A and the second sheet layer 20B are bonded to each other with the molten and solidified material 20m of a part of the first sheet layer 20A and the second sheet layer 20B and the molten and solidified material 30m of the entire part or a most part of the elastic film 30 in the bonded portion 40. Note that in the third welding form illustrated in FIG. 19(b), the molten and solidified material 30m of the elastic film 30 represented in white is observed between the molten and solidified materials 20m of the first sheet layer 20A or the second sheet layer 20B represented in black, whereas in the first welding form illustrated in FIG. 19(a), a molten and solidified material of the elastic film is not observed between the molten and solidified materials 20m of the first sheet layer 20A or the second sheet layer 20B (white portion represents a boundary of the molten and solidified material 20m and irregular reflection of the molten and solidified material 20m).

As in the first adhesion form and the third adhesion form, when the first sheet layer 20A and the second sheet layer 20B are bonded to each other using the molten and solidified material 20m of a most part or a part of at least one of the first sheet layer 20A and the second sheet layer 20B as an adhesive, it is preferable not to melt a part of the first sheet layer 20A and the second sheet layer 20B because the bonded portion 40 is not hardened. Note that when the first sheet layer 20A and the second sheet layer 20B are formed of a nonwoven fabric, a form in which a part of the first sheet layer 20A and the second sheet layer 20B does not melt includes a form in which cores (including not only a core in a composite fiber but also a center portion of a single component fiber) of all the fibers of the bonded portion 40 remain unmelted but portions surrounding the cores (including not only a sheath in a composite fiber but also a portion on a surface layer side of a single component fiber) melt, and a form in which some fibers do not melt at all, but all the remaining fibers melt or cores thereof remain unmelted but portions surrounding the cores melt.

When the first sheet layer 20A and the second sheet layer 20B are bonded to each other using the molten and solidified material 30m of the elastic film 30 as an adhesive as in the second welding form and the third welding form, peel strength is high. In the second welding form, manufacture is possible by sandwiching the elastic film 30 between the first sheet layer 20A and the second sheet layer 20B under a condition that the melting point of at least one of the first sheet layer 20A and the second sheet layer 20B is higher than the melting point of the elastic film 30 and the heating temperature at the time of forming the bonded portion 40, pressurizing and heating a site to be the bonded portion 40, and melting only the elastic film 30. Meanwhile, in the third welding form, manufacture is possible by sandwiching the elastic film 30 between the first sheet layer 20A and the second sheet layer 20B under a condition that the melting point of at least one of the first sheet layer 20A and the second sheet layer 20B is higher than the melting point of the elastic film 30, pressurizing and heating a site to be the bonded portion 40, and melting at least one of the first sheet layer 20A and the second sheet layer 20B and the elastic film 30. From such a viewpoint, the elastic film 30 preferably has a melting point of about 80 to 145° C., the first sheet layer 20A and the second sheet layer 20B each have a melting point preferably of about 85 to 190° C., particularly preferably of 150 to 190° C., and a difference between the melting point of each of the first sheet layer 20A and the second sheet layer 20B and the melting point of the elastic film 30 is preferably about 60 to 90° C. The heating temperature is preferably about 100 to 150° C.

Figure 18A:
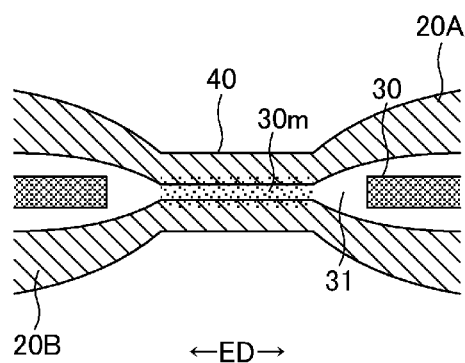
FIGS. 18a-18c are cross-sectional views schematically illustrating a cross-section of a main part of an outer member that has stretched to some extent.
Figure 18B:
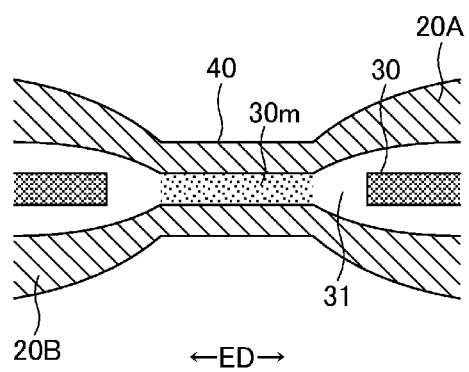
Figure 18C:
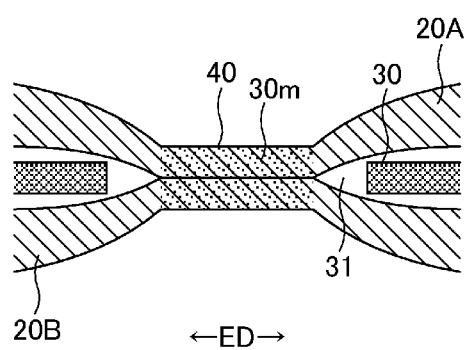

In the second welding form and the third welding form, when the first sheet layer 20A and the second sheet layer 20B are formed of a nonwoven fabric, the molten and solidified material 30m of the elastic film 30 may penetrate between fibers over the entire thickness direction of the first sheet layer 20A and the second sheet layer 20B in the bonded portion 40 as illustrated in FIG. 18(c). However, a form in which the molten and solidified material 30m penetrates between fibers up to an intermediate portion in the thickness direction as illustrated in FIGS. 17(b), 17(c), and 18(a), or a form in which the molten and solidified material 30m hardly penetrates between fibers of the first sheet layer 20A and the second sheet layer 20B as illustrated in FIG. 18(b) achieves higher flexibility of the bonded portion 40.

FIGS. 21 and 22 illustrate an example of an ultrasonic sealing device suitable for forming the second welding form and the third welding form. In this ultrasonic sealing device, for forming the bonded portion 40, the first sheet layer 20A, the elastic film 30, and the second sheet layer 20B are fed between an anvil roll 60 having protrusions 60a formed in the pattern of the bonded portions 40 on an outer surface thereof and an ultrasonic horn 61. At this time, for example, by making a feeding transfer speed of the elastic film 30 by a feeding drive roll 63 and a nip roll 62 on an upstream side slower than the feeding speed after the anvil roll 60 and the ultrasonic horn 61, the elastic film 30 is stretched to a predetermined stretch rate in the MD direction (machine direction, flow direction) in a path from a nip position by the feeding drive roll 63 and the nip roll 62 to a seal position by the anvil roll 60 and the ultrasonic horn 61. The stretch rate of the elastic film 30 can be set by selecting a speed difference between the anvil roll 60 and the feeding drive roll 63, and can be set to about 300% to 500%, for example. Reference numeral 62 represents a nip roll. The first sheet layer 20A, the elastic film 30, and the second sheet layer 20B fed between the anvil roll 60 and the ultrasonic horn 61 are pressurized between the protrusions 60a and the ultrasonic horn 61 and heated by ultrasonic vibration energy of the ultrasonic horn 61 while the first sheet layer 20A, the elastic film 30, and the second sheet layer 20B are laminated in this order to melt only the elastic film 30 or to melt at least one of the first sheet layer 20A and the second sheet layer 20B and the elastic film 30. As a result, the through-holes 31 are formed in the elastic film 30, and simultaneously the first sheet layer 20A and the second sheet layer 20B are bonded to each other through the through-holes 31. Therefore, in this case, by selecting the sizes, the shapes, a separation interval, an arrangement pattern in a roll length direction and roll circumferential direction, and the like of the protrusions 60a of the anvil roll 60, the area ratio of the bonded portions 40 can be selected.

A reason why the through-holes 31 are formed is not necessarily clear, but is considered to be that portions corresponding to the protrusions 60a of the anvil roll 60 in the elastic film 30 are melted and detached from the surroundings to form holes. At this time, a portion of the elastic film 30 between the adjacent through-holes 31 in the stretchable direction ED is cut from both sides in the stretchable direction by the through-holes 31 as illustrated in FIGS. 7(*a*), 9(*a*), and 11(*a*), and loses a support on both sides in a contraction direction. Therefore, the portion of the elastic film 30 between the adjacent through-holes 31 in the stretchable direction ED contracts until the center side of the orthogonal direction XD is balanced with the central side of the stretchable direction within a range in which continuity in a direction orthogonal to the contraction direction can be maintained, and the through-holes 31 expand in the stretchable direction ED. Then, when the bonded portions 40 are formed in a pattern in which a portion where the elastic film 30 is linearly continuous in the stretchable direction ED remains as in a stretchable region 80 described later, as illustrated in FIGS. 7(*d*) and 9(*d*), when contraction occurs to a natural length state, for example, by cutting the elastic film 30 into individual products, the length of the expanded portion of the through-hole 31 in the stretchable direction ED contracts until a gap is not formed between the through-hole 31 and the bonded portion 40. Meanwhile, when the bonded portions 40 are formed in a pattern in which a portion where the elastic film 30 is linearly continuous in the stretchable direction ED is not present as in a non-stretchable region 70 described later, as illustrated in FIG. 11(*d*), when contraction occurs to a natural length state, for example, by cutting the elastic film 30 into individual products, the length of the expanded portion of the through-hole 31 in the stretchable direction ED hardly contracts. Therefore, a large gap remains between the through-hole 31 and the bonded portion 40.

A material constituting the first sheet layer 20A and the second sheet layer 20B can be used without particular limitation as long as having a sheet shape. However, a nonwoven fabric is preferably used from viewpoints of air permeability and flexibility. The nonwoven fabric is not particularly limited concerning a raw material fiber thereof. Examples thereof include a synthetic fiber such as a polyolefin-based fiber including polyethylene and polypropylene, a polyester-based fiber, or a polyamide-based fiber, a regenerated fiber such as rayon or cupra, a natural fiber such as cotton, and a mixed fiber and a composite fiber in which two or more kinds of these fibers are used. Furthermore, the nonwoven fabric may be manufactured by any processing. Examples of a processing method include a known method such as a spunlace method, a spunbond method, a thermal bond method, a melt blown method, a needle punch method, an air through method, and a point bond method. In a case where a nonwoven fabric is used, the nonwoven fabric preferably has a basis weight of about 12 to 20 g/m$^2$. Furthermore, a part or the entire part of the first sheet layer 20A and the second sheet layer 20B may be a pair of facing layers obtained by folding back a single material. For example, as in the illustrated embodiment, in the waist portion 23, by using a constituent material located outside as the second sheet layer 20B, and using a folded-back portion 20C obtained by folding back a waist opening edge thereof to an internal surface side as the first sheet layer 20A, the elastic film 30 can be interposed therebetween. Moreover, in a portion other than the waist portion 23, by using a constituent material located inside as the first sheet layer 20A, and using a constituent material located outside as the second sheet layer 20B, the elastic film 30 can be interposed therebetween. Of course, by disposing the constituent material of the first sheet layer 20A and the constituent material of the second sheet layer 20B individually over the entire front-back direction LD without folding back the constituent materials, the elastic film 30 can also be interposed between the constituent material of the first sheet layer 20A and the constituent material of the second sheet layer 20B.

The elastic film 30 is not particularly limited, and can be a non-porous film or a film having many holes and slits for air permeation as long as being a thermoplastic resin film having elasticity in itself. Particularly, the elastic film 30 preferably has a tensile strength of 8 to 25 N/35 mm in the width direction WD (stretchable direction ED, MD direction), a tensile strength of 5 to 20 N/35 mm in the front-back direction LD (orthogonal direction XD, CD direction), a tensile elongation of 450 to 1050% in the width direction WD, and a tensile elongation of 450 to 1400% in the front-back direction LD. The thickness of the elastic film 30 is not particularly limited, but is preferably about 20 to 40 μm.

(Stretchable Region)

A region having the elastic film stretchable structure 20X in the outer member 20 can stretch and contract in the width direction WD. In other words, the region has a stretchable region that contracts in the width direction WD by a contraction force of the elastic film 30 in a natural length state and is extensible in the width direction WD at the time of wearing. Such a stretchable region can be formed by bonding the first sheet layer 20A and the second sheet layer 20B to each other through the through-holes 31 of the elastic film 30 at many places with intervals in a state where the elastic film 30 is stretched in the width direction WD. In order to exhibit sufficient elasticity, the through-holes 31 and the bonded portions are preferably disposed at intervals in the width direction WD and the front-back direction LD (orthogonal direction XD) orthogonal thereto so as to have a portion 32 where the elastic film 30 is linearly continuous in the width direction WD.

Figure 7A:
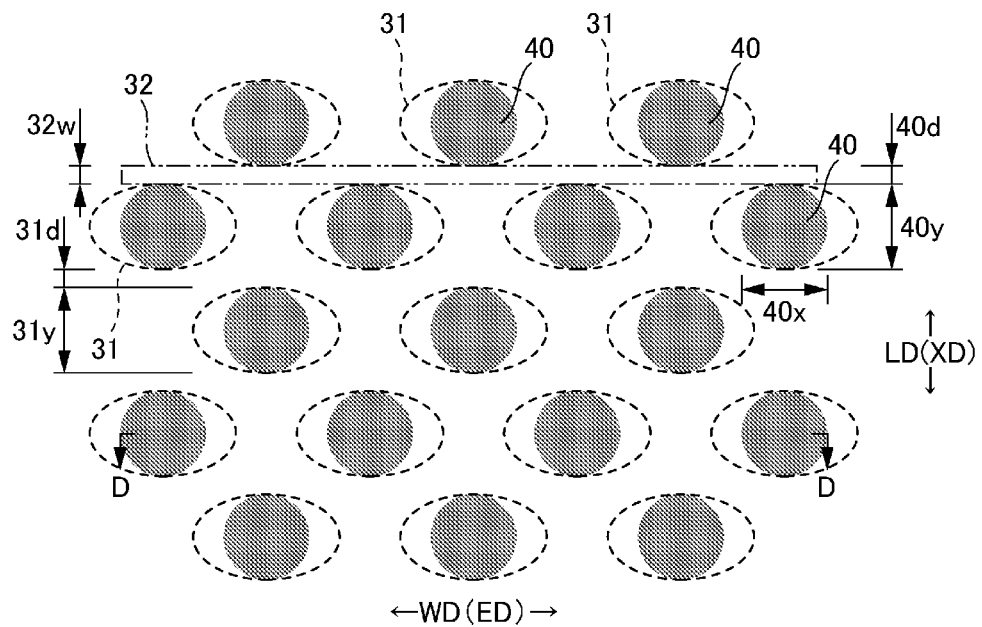
FIG. 7(a) is a plan view of a main part of a stretchable region.
Figure 7B:
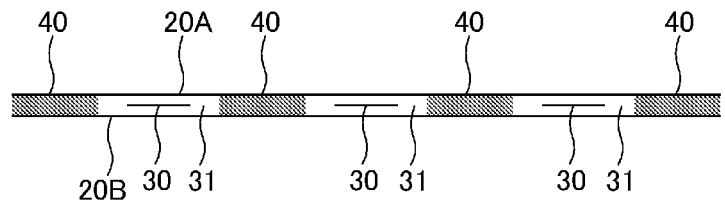
FIG. 7(b) is a cross-sectional view taken along line D-D in FIG. 7(a)
Figure 7C:
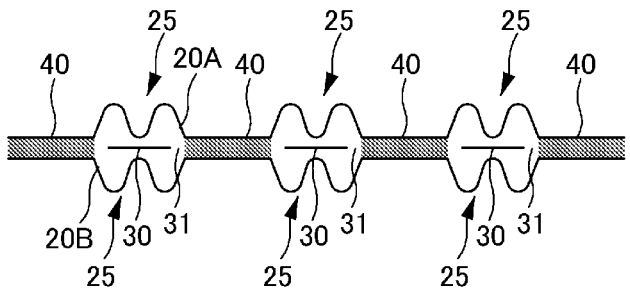
FIG. 7(c) is a cross-sectional view in a wearing state.
Figure 7D:
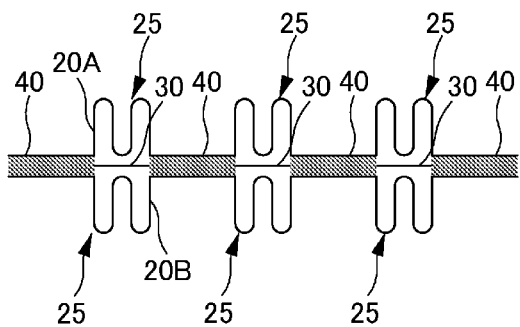
FIG. 7(d) is a cross-sectional view in a natural length state.
Figure 8A:
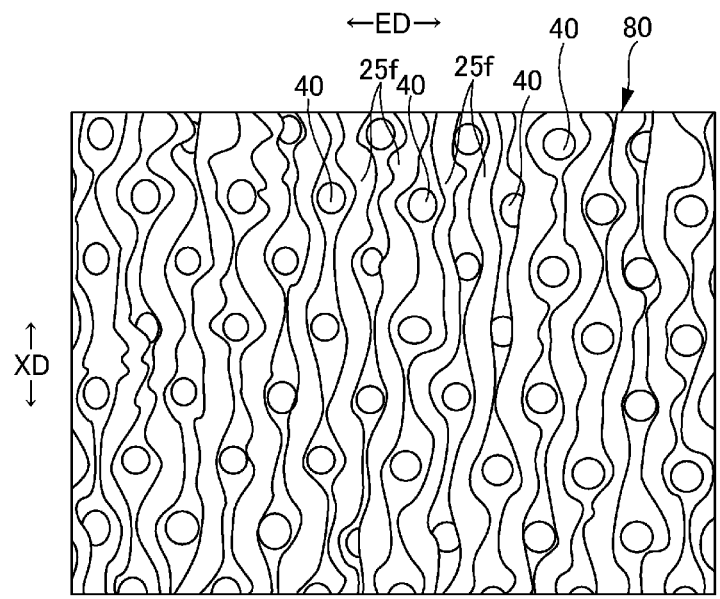
FIG. 8(a) is a trace view of a micrograph of a stretchable region of a sample, taken from a plane direction.
Figure 8B:
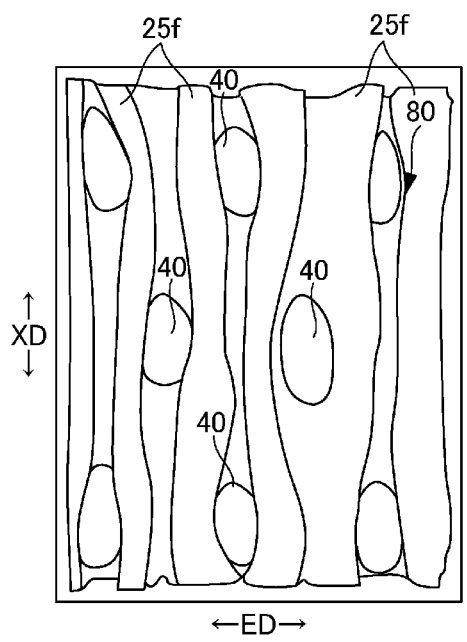
FIG. 8(b) is a trace view of a high magnification micrograph of a stretchable region of a sample, taken from a plane direction.
Figure 8C:
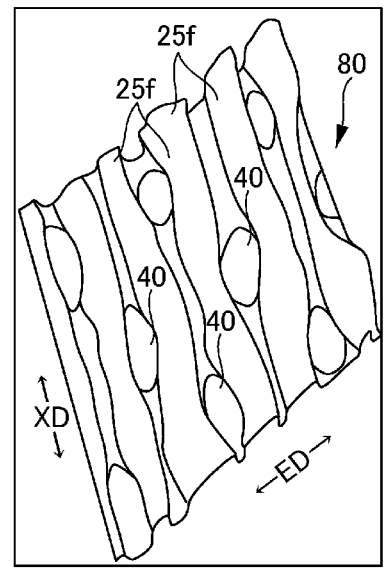
FIG. 8(c) is a trace view of a high magnification micrograph of a stretchable region of a sample, taken from a perspective direction.
Figure 9A:
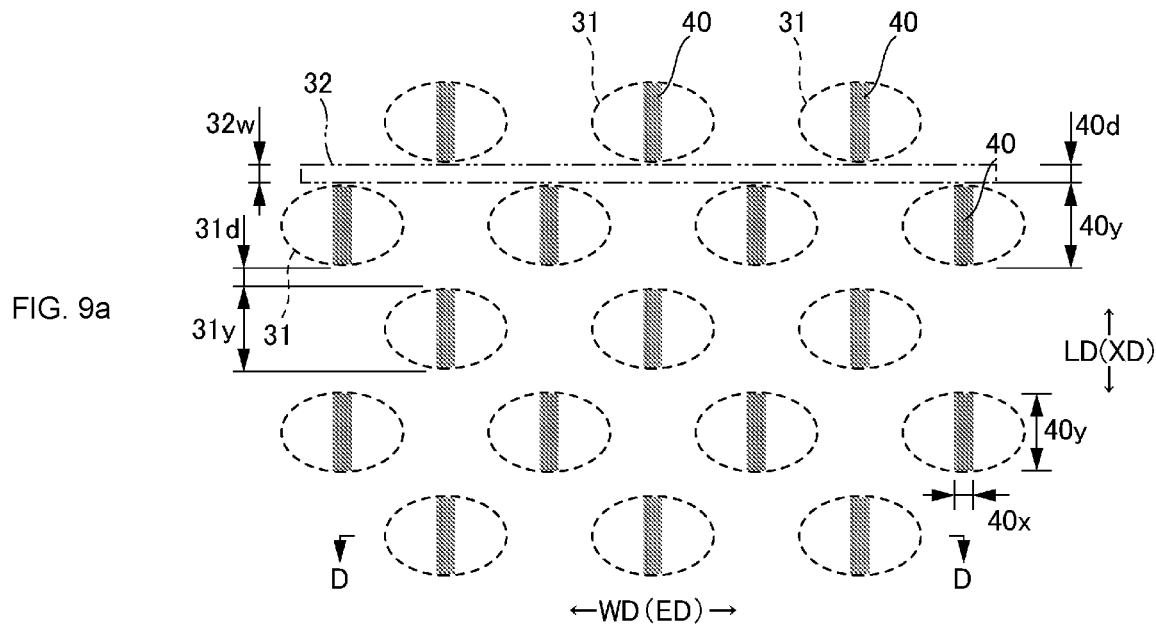
FIG. 9(a) is a plan view of a main part of a stretchable region.
Figure 9B:
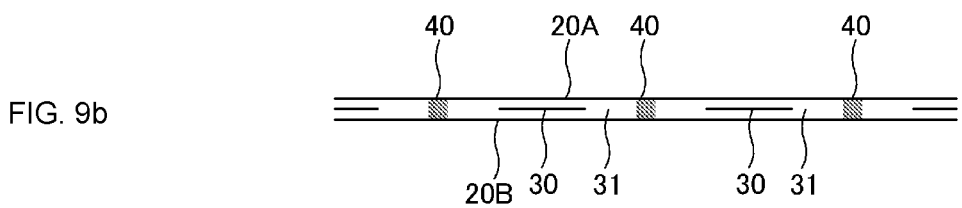
FIG. 9(b) is a cross-sectional view taken along line D-D in FIG. 9(a)
Figure 9C:
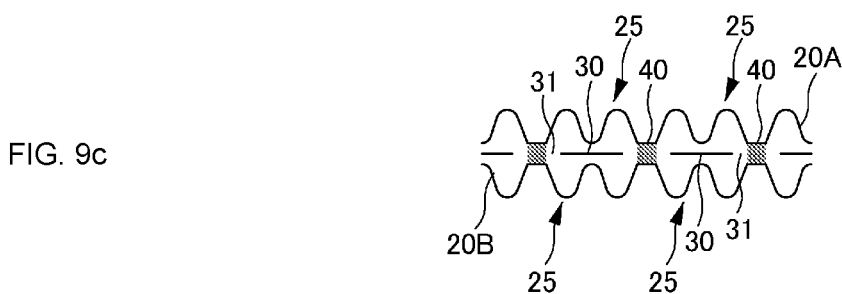
FIG. 9(c) is a cross-sectional view in a wearing state.
Figure 9D:
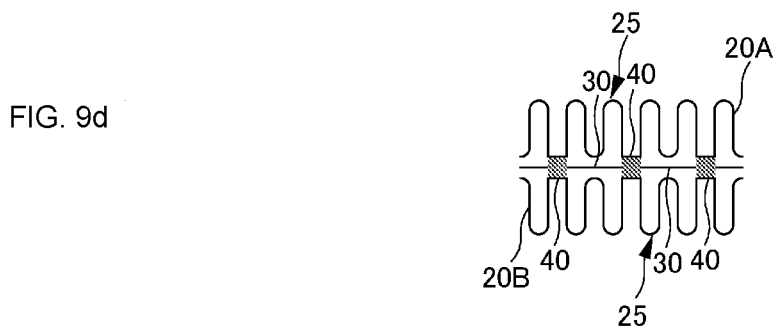
FIG. 9(d) is a cross-sectional view in a natural length state.
Figure 10A:
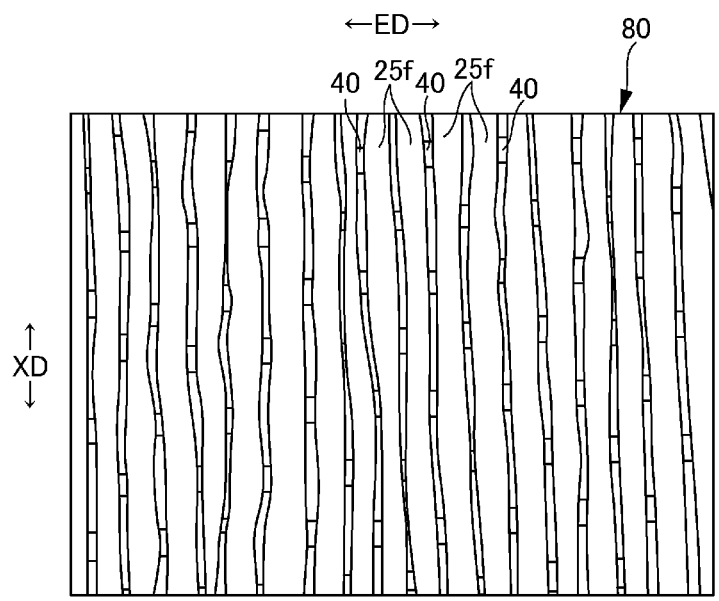
FIG. 10(a) is a trace view of a micrograph of a stretchable region of a sample, taken from a plane direction.
Figure 10B:
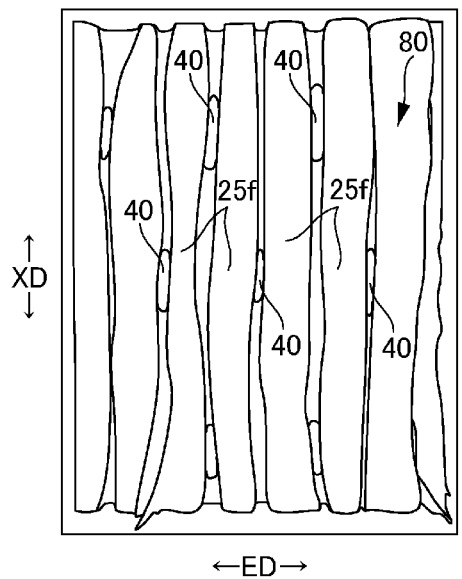
FIG. 10(b) is a trace view of a high magnification micrograph of a stretchable region of a sample, taken from a plane direction.
Figure 10C:
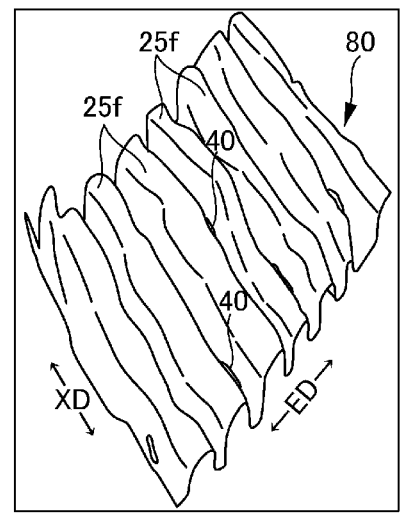
FIG. 10(c) is a trace view of a high magnification micrograph of a stretchable region of a sample, taken from a perspective direction.
Figure 11A:
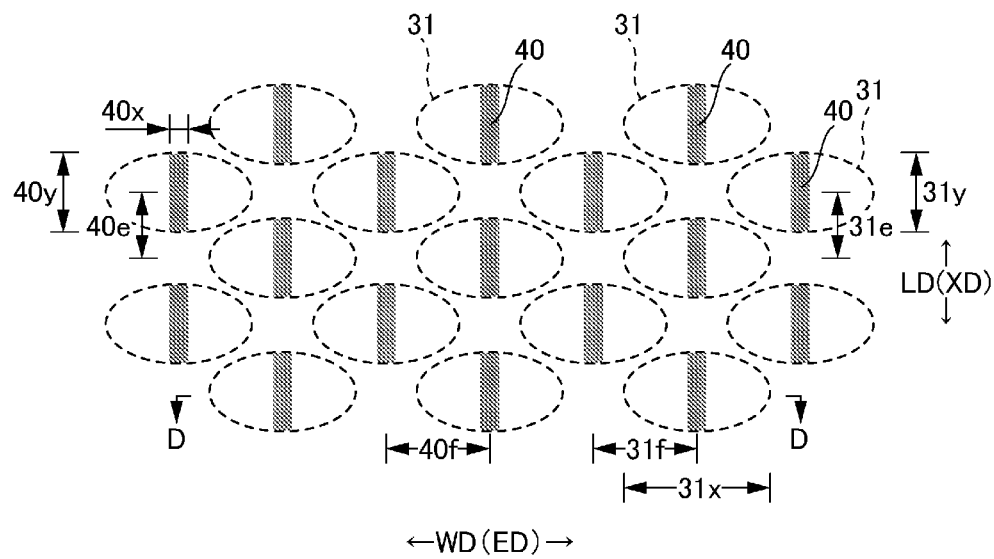
FIG. 11(a) is a plan view of a main part of a non-stretchable region.
Figure 11B:
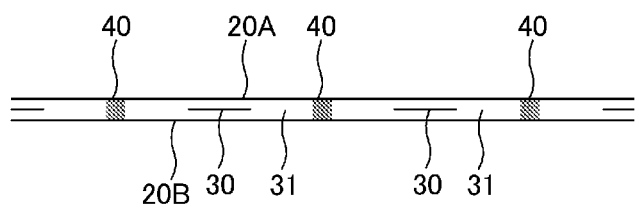
FIG. 11(b) is a cross-sectional view taken along line D-D in FIG. 11(a)
Figure 11C:
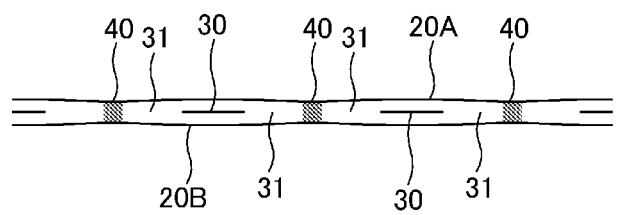
FIG. 11(c) is a cross-sectional view in a wearing state.
Figure 11D:
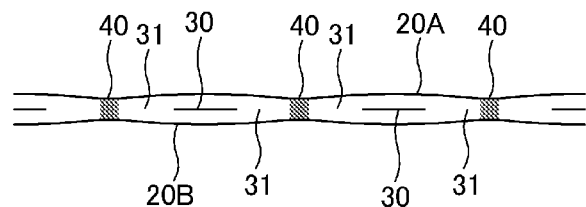
FIG. 11(d) is a cross-sectional view in a natural length state.

In a natural length state, as illustrated in FIGS. 7(d) and 9(d), the stretchable region 80 swells in a direction in which the first sheet layer 20A and the second sheet layer 20B between the bonded portions 40 are separated from each other, and contraction wrinkles 25 extending in the front-back direction LD are formed. As illustrated in FIGS. 7(c) and 9(c), the contraction wrinkles 25 are stretched but remain even in a wearing state in which the stretchable region 80 stretches to some extent in the width direction WD. As in the illustrated embodiment, when the first sheet layer 20A and the second sheet layer 20B are not bonded to the elastic film 30 except for at least a portion between the first sheet layer 20A and the second sheet layer 20B in the bonded portion 40, as can be seen from FIGS. 7(c) and 9(c) assuming a wearing state and FIGS. 7(a), 7(b), 9(a), and 9(b) assuming unfolded states of the first sheet layer 20A and the second sheet layer 20B, in these states, a gap is formed between the through-hole 31 in the elastic film 30 and the bonded portion 40, and air permeability is imparted by this gap even if a material of the elastic film 30 is a non-porous film or sheet. In a natural length state illustrated in FIGS. 7(d) and 9(d), the through-hole 31 is narrowed by contraction of the elastic film 30, and a gap is hardly formed between the through-hole 31 and the bonded portion 40. Note that the state of the contraction wrinkles 25 in a wearing state and in a natural length state also appears in FIGS. 8 and 10.

It is desirable that the elongation at elastic limit of the stretchable region 80 in the width direction WD is 200% or more (preferably 265 to 295%). The elongation at elastic limit of the stretchable region 80 is substantially determined by the stretch rate of the elastic film 30 at the time of manufacture, but decreases due to factors that inhibit contraction in the width direction WD on the basis of the stretch rate. A main one of such inhibition factors is the ratio of the length $40x$ of the bonded portion 40 with respect to unit length in the width direction WD. The larger this ratio is, the lower the elongation at elastic limit is. In a normal case, the length $40x$ of the bonded portion 40 has a correlation with the area ratio of the bonded portions 40. Therefore, the elongation at elastic limit of the stretchable region 80 can be adjusted by the area ratio of the bonded portions 40.

A stretch stress of the stretchable region 80 can be adjusted mainly by the sum of the widths $32w$ of the portions 32 where the elastic film 30 is linearly continuous in the width direction WD. The width $32w$ of the portion 32 where the elastic film 30 is linearly continuous in the width direction WD is equal to an interval $31d$ between the through-holes 31 in contact with both side edges of the continuous portion 32 in the front-back direction LD. The interval $31d$ between the through-holes 31 is equal to an interval $40d$ between the bonded portions 40 in contact with both side edges of the continuous portion in the front-back direction LD when the length $31y$ of the through-hole 31 in the front-back direction LD is equal to the length $40y$ of the bonded portion 40 in the front-back direction LD (for example, when the above-described method for simultaneously forming the through-holes 31 and the bonded portions 40 is adopted). Therefore, in this case, the stretch stress of the stretchable region 80 can be adjusted by the ratio of the length $40y$ of the bonded portion 40 with respect to unit length in the front-back direction LD. In a normal case, the length $40y$ of the bonded portion 40 has a correlation with the area ratio of the bonded portions 40. Therefore, the stretch stress of the stretchable region 80 can be adjusted by the area ratio of the bonded portions 40. A stretch stress at the time of stretch to 50% of the elastic limit can be taken as a standard of the stretch stress of the stretchable region 80.

The area ratio of the bonded portions 40 and the area of each of the bonded portions 40 in the stretchable region 80 can be determined appropriately, but are preferably within the following ranges in a normal case.

Area of bonded portion 40: 0.14 to 3.5 mm$^2$ (particularly 0.14 to 1.0 mm$^2$)

Area ratio of bonded portions 40: 1.8 to 19.1% (particularly 1.8 to 10.6%)

As described above, the elongation at elastic limit and the stretch stress of the stretchable region 80 can be adjusted by the area of the bonded portion 40. Therefore, not by making the pattern of the bonded portions 40 in the stretchable region 80 uniform as illustrated in FIG. 2, but by disposing a plurality of regions having different area ratios of the bonded portions 40 in the stretchable region 80 as illustrated in FIG. 15, fitting can be changed according to a site. In the form illustrated in FIG. 15, a region 81 extending obliquely along a root of a leg in the front body F and an edge region 82 of a leg opening each have a higher area ratio of the bonded portions 40 than the other regions, and therefore has a weak stretch stress and stretches and contracts flexibly. An ilium facing region 83 in the back body B and the edge region 82 of the leg opening also each have a higher area ratio of the bonded portions 40 than the other regions, and therefore have a weak stretch stress and stretches and contracts flexibly. In the illustrated example, a region 84 that is an intermediate portion of a portion overlapping with the inner member 10 in the front body F in the width direction WD has a still higher area ratio of the sheet bonded portions 40 than the other regions, and has a still weaker stretch stress and still smaller elongation at elastic limit.

(Non-Stretchable Region)

In the example illustrated in FIG. 2, the entire stretchable structure 20X of the elastic film 30 is set to the stretchable region 80, and a non-stretchable region is not included. However, in a region having the elastic film stretchable structure 20X, as illustrated in FIG. 15, a non-stretchable region 70 can be disposed, for example, on at least one side of the stretchable region 80 in the width direction. Arrangement of the stretchable region 80 and the non-stretchable region 70 can be determined appropriately. In a case of the outer member 20 of the underpants-type disposable diaper as in the present embodiment, a portion overlapping with the absorber 13 is a region that does not need to stretch or contract. Therefore, as in the illustrated embodiment, a part or the entire part of a portion overlapping with the absorber 13 (desirably including almost an entire inner and outer fixed region 10B) is preferably set to the non-stretchable region 70. Of course, the non-stretchable region 70 can be disposed from a region overlapping with the absorber 13 to a region not overlapping with the absorber 13 located in the width direction WD or the front-back direction LD, or can be disposed only in the region not overlapping with the absorber 13.

The non-stretchable region 70 is a region in which the elastic film 30 is continuous in the width direction WD but which does not have a linearly continuous portion in the width direction WD due to the presence of the through-hole 31. Therefore, in a state where the elastic film 30 stretches in the width direction WD, even if the entire elastic film stretchable structure 20X including both the stretchable region 80 and the non-stretchable region 70 is formed by bonding the first sheet layer 20A and the second sheet layer 20B to each other through the through-holes 31 of the elastic film 30 at intervals in the width direction WD and the front-back direction LD orthogonal thereto to form the many bonded portions 40, as illustrated in FIG. 11, in the non-stretchable region 70, the elastic film 30 is not linearly continuous in the width direction WD. Therefore, a contraction force of the elastic film 30 hardly acts on the first sheet layer 20A and the second sheet layer 20B, elasticity almost disappears, and an elongation at elastic limit is close to 100%. In such a non-stretchable region 70, the first sheet layer 20A and the second sheet layer 20B are bonded to each other with many bonded portions 40 arranged at intervals, and the bonded portions 40 are not continuous. Therefore, reduction in flexibility is prevented. In other words, the stretchable region 80 and the non-stretchable region 70 can be formed by presence or absence of a portion where the elastic film 30 is not linearly continuous in the width direction WD. In addition, continuity of the elastic film 30 remains even in the non-stretchable region 70. As can be seen from FIG. 12, an independent cut piece of the elastic film 30 does not remain, and wrinkles are not formed. Therefore, appearance is very good, and air permeability in the thickness direction due to the through-holes 31 is ensured. The non-stretchable region 70 preferably has an elongation at elastic limit of 120% or less (preferably 110% or less, more preferably 100%) in the width direction WD.

An arrangement pattern of the through-holes 31 in the elastic film 30 in the non-stretchable region 70 can be determined appropriately. However, when a zigzag arrangement is formed as illustrated in FIG. 11, and a pattern in which a central interval 31e between the through-holes 31 in the front-back direction LD is shorter than the length 31y of the through-hole 31 in the front-back direction LD is formed, linear continuity in the width direction WD can be almost completely eliminated while continuity of the elastic film 30 is maintained, and appearance is also preferable as illustrated in FIG. 12. In this case, a central interval 31f between the through-holes 31 in the width direction WD is more preferably shorter than a length 31x of the through-hole 31 in the width direction WD.

In a normal case, particularly in a case where the elastic film 30 has a stretch stress of 4 to 12 N/35 mm when the elastic film 30 is stretched four times in the width direction WD, in a state where the non-stretchable region 70 is stretched to an elastic limit in the width direction WD, the central interval 31e between the through-holes 31 in the front-back direction LD is preferably 0.4 to 2.7 mm, and the length 31y of the through-hole 31 in the front-back direction LD is preferably 0.5 to 3.0 mm, and particularly preferably 0.7 to 1.1 mm. The central interval 31f between the through-holes 31 in the width direction WD is preferably 0.5 to 2 times, and particularly preferably 1 to 1.2 times the length 31y of the through-hole 31 in the front-back direction LD. The length 31x of the through-hole 31 in the width direction WD is preferably 1.1 to 1.8 times, and particularly preferably 1.1 to 1.4 times the central interval 31f between the through-holes 31 in the width direction WD. Note that in a state where the non-stretchable region 70 is stretched to an elastic limit in the width direction WD (in other words, in a state where the first sheet layer 20A and the second sheet layer 20B are completely unfolded), the central interval 31f between the through-holes 31 in the width direction WD is equal to a central interval 40f between the bonded portions 40 in the width direction WD, the central interval 31e between the through-holes 31 in the front-back direction LD is equal to a central interval 40e between the bonded portions 40 in the front-back direction LD, and the length 31y of the through-hole 31 in the front-back direction LD is equal to the length 40y of the bonded portion 40 in the front-back direction LD.

In the non-stretchable region 70, when the first sheet layer 20A and the second sheet layer 20B are not bonded to the elastic film 30 except for a portion between the first sheet layer 20A and the second sheet layer 20B in the bonded portion 40, and a gap is formed by separating a peripheral edge of the through-hole 31 of the elastic film 30 from the bonded portion 40 on both sides of the bonded portion 40 in the width direction in a natural length state, this gap imparts air permeability all the time even if a material of the elastic film 30 is a non-porous film or sheet. Therefore, this is preferable. When the above-described method for simultaneously forming the through-holes 31 and the bonded portions 40 is adopted, this state naturally occurs regardless of the shapes of the bonded portions 40 and the like.

Figure 13D:
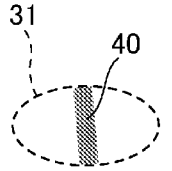

The shape of each of the bonded portions 40 and the through-holes 31 in a natural length state is not particularly limited. However, each of the bonded portions 40 and the through-holes 31 in a natural length state desirably has a small area from a viewpoint of flexibility. In order to eliminate linear continuity of the elastic film 30 in the width direction WD, a shape that is long in the front-back direction LD is desirable. Therefore, an ellipse, a rectangle (see FIGS. 11 and 13(d)), a rhombus (see FIG. 13(b)), a convex lens shape (see FIG. 13(b)), and a concave lens shape (see FIG. 13(c)) which are long in the front-back direction LD are preferable. However, if the shape has a corner with an acute angle like a rhombus, the elastic film 30 is easily broken. Meanwhile, a convex lens shape is preferable because welding of the bonded portion 40 is stable, and a concave lens shape is preferable because the area can be further reduced.

The area ratio of the bonded portions 40 and the area of each of the bonded portions 40 in the non-stretchable region can determined be appropriately, but are preferably within the following range in a normal case because the non-stretchable region 70 does not become hard due to a small area of each of the bonded portions 40 and a low area ratio of the bonded portions 40.

Area of bonded portion 40: 0.10 to 0.75 mm$^2$ (particularly 0.10 to 0.35 mm$^2$)

Area ratio of bonded portions 40: 4 to 13% (particularly 5 to 10%)

As described above, the elongation at elastic limit of the non-stretchable region 70 can be changed according to the arrangement pattern of the through-holes 31, the size of each of the through-holes 31, and the central interval therebetween. Therefore, although not illustrated, the arrangement pattern of the through-holes 31, the size of each of the through-holes 31, and the central interval therebetween can be made different among a plurality of places in the stretchable region 80 or among the plurality of non-stretchable regions 70. For example, it is one preferable form to make the elongation at elastic limit in the non-stretchable region 70 of the front body F larger than the elongation at elastic limit in the non-stretchable region 70 of the back body B.

The non-stretchable region 70 can also adopt another form that cancels elasticity, such as a form in which the non-stretchable region 70 has a linearly continuous portion in the width direction WD like the stretchable region, but the elongation at elastic limit is significantly low because the area ratio of the bonded portions 40 is higher than that in the stretchable region, and the elongation at elastic limit is specifically 130% or less, or a form in which the elastic film 30 is cut at one place or a plurality of places in the width direction WD like a conventional stretchable structure using a rubber thread.

(Overlapping Portion of Elastic Film)

Characteristically, the stretchable region 80 includes the plurality of elastic films 30 disposed so as to have an overlapping portion 33. The number of laminated layers of the elastic films 30 in a first region 26 located in an intermediate portion of the stretchable region 80 in the front-back direction LD (orthogonal direction XD) is different from that in each of second regions 27 adjacent to both sides of the first region 26. As a result, the number of laminated layers of the elastic films 30 is different between the first region 26 and the second region 27. Therefore, a contraction force at the time of stretch can be made different regardless of a change in the pattern of the bonded portion 40 or the stretch rate of the elastic film 30. That is, if the first region 26 and the second region 27 have the same pattern of the bonded portions 40 and the same stretch rate of the elastic film 30, a contraction force in a region with a large number of laminated layers is relatively stronger, and a contraction force in a region with a small number of laminated layers is relatively weaker.

In manufacture, for example, as illustrated in FIGS. 21 and 22, the plurality of elastic films 30 is fed between the anvil roll 60 and the ultrasonic horn 61 so as to have the overlapping portion 33, and the first sheet layer 20A and the second sheet layer 20B can be bonded to each other.

Either the first region 26 or the second region 27 may have a larger number of laminated layers of the elastic films 30. As in the examples illustrated in FIGS. 1, 2, and 4, and the examples illustrated in FIGS. 15 and 16, a structure is preferable in which one stretchable region 80 includes the elastic film 30 extending from one of the second regions 27 to the first region 26, and the elastic film 30 extending from the other second region 27 to the first region 26, each of the second regions 27 includes only one elastic film 30, and the first region 26 includes two elastic films 30 overlapping with each other. In this case, a simple structure in which the number of elastic films 30 per stretchable region 80 is the minimum two, and the number of laminated layers of the elastic films 30 is also minimum is obtained. Therefore, a risk of making manufacture difficult, such as difficulty in forming the bonded portions 40, is reduced. As in the example illustrated in FIG. 23, when three or more elastic films 30 are used per stretchable region 80, a contraction force can be changed so as to be suitable for more sites. In the example illustrated in FIG. 23, the elastic film 30 over the entire stretchable region 80 is basically used, and the elastic film 30 is added to a site where a strong contraction force should be exerted, that is, to one intermediate portion in the front-back direction LD and an end portion in the front-back direction LD (the waist portion 23 in the illustrated example, but the elastic film 30 may be disposed at an end portion of a leg opening side instead of the waist portion 23 or together with the waist portion 23). However, the elastic film 30 can be added to a plurality of places in an intermediate portion in the front-back direction LD.

When the plurality of elastic films 30 is used and the number of laminated layers of the elastic films 30 is changed depending on a site as described above, unlike a conventional form in which the number of laminated layers is increased by folding, the number of portions with a large number of laminated layers and arrangement thereof are not limited, and various changes are possible. For example, as in the example illustrated in FIGS. 1, 2 and 4, and the example illustrated in FIGS. 15 and 16, when the outer member 20 of the front body F has the stretchable region 80 at least in the lower torso portion T, the outer member 20 of the back body B has the stretchable region 80 extending from the lower torso portion T to the intermediate portion L, and a contraction force of each of the stretchable regions 80 is changed in the front-back direction LD by the two elastic films 30 consisting of the elastic film 30 located on the waist opening side and the elastic film 30 located on the opposite side (center side of the diaper in the front-back direction), as illustrated in FIG. 14, preferably, the stretchable region 80 of the outer member 20 of the front body F has the first region 26 in the lower torso portion T and has the second region 27 in the other regions, and the stretchable region 80 of the outer member 20 of the back body B has the first region 26 in the intermediate portion L and has the second region 27 in the other regions. By disposing the first region 26 in which the two elastic films 30 overlap with each other and the second region 27 including only one elastic film 30 asymmetrically in a front-back direction as described above, favorable fitting to a lower abdomen portion and a lower gluteal region (gluteal groove) where a gap is easily generated is achieved. In addition, since the position of the first region 26 of the front body F is different from the first region 26 of the back body B in the side seal portion 21, the number of laminated layers of a material in the side seal portion 21 does not become locally too large. Therefore, deterioration of wearing feeling and sealing failure of the side seal portion 21 are prevented.

As the plurality of elastic films 30 disposed in one stretchable region 80, elastic films having the same stretch stress may be used. However, when elastic films having different stretch stresses are used, a contraction force can be changed at three or more stages together with a change in the number of laminated layers. For example, as the elastic films 30 in the examples illustrated in FIGS. 1, 2, and 4, and in the examples illustrated in FIGS. 15 and 16, when elastic films 30 having different stretch stresses at the time of 4-times stretch in the width direction WD are used, a contraction force can be made different among the three regions consisting of one of the second regions 27, the first region 26, and the other second region 27 while a simple structure is maintained. Particularly, if the elastic film 30 located on the waist opening side has a weaker stretch stress at the time of 4-times stretch in the stretchable direction ED than the elastic film 30 located on the opposite side (center side of the diaper in the front-back direction), a portion where a gap is easily generated can be firmly tightened at the time of wearing, and a contraction force of a portion closer to a waist opening than the portion where a gap is easily generated can be minimized to reduce tightening feeling on the waist opening side. Therefore, this is preferable.

A case where an elongation at elastic limit of the one of the second regions 27 is different from that of the other second region 27, and the larger elongation at elastic limit is the same as the elongation at elastic limit of the first region 26 is also preferable. Such a structure having different elongation at elastic limits can be formed by making the stretch rates of the respective elastic films 30 different when the first sheet layer 20A and the second sheet layer 20B are bonded to each other in manufacture. For example, as in a sheet bonding device illustrated in FIGS. 21 and 22, if the feeding drive roll 63 and the nip roll 62 are disposed independently with respect to each of the elastic films 30, and feeding transfer speeds of the elastic films 30 feeding to the anvil roll 60 and the ultrasonic horn 61 are made different from one another, the elongation at elastic limit of one of the second regions 27 is different from that of the other second region 27, and the larger elongation at elastic limit is the same as the elongation at elastic limit of the first region 26.

In this structure with different elongation at elastic limits, when the stretchable region 80 is stretched in the width direction WD from an initial stage at which both the elastic films 30 are in a natural length state, the stretchable region 80 comes to a wearing stage at which both the elastic films 30 are in a stretched state through an intermediate stage at which one of the elastic films 30 is in a natural length state, and the other elastic film 30 is in a stretched state. Therefore, when the stretchable region 80 is stretched for wearing, the first region 26 initially stretches with the same stretch stress as the second region 27 with a larger elongation at elastic limit, and the stretch stress is the strongest at a wearing stage. Therefore, the diaper is easily worn, and obtains firm fitting in a wearing state.

In the structure with different elongation at elastic limits, the elastic films 30 having different stretch stresses can be used, but the elastic films 30 having the same stretch stress can also be used. The latter is more advantageous than the former from a viewpoint of material cost.

(Others)

The above-described stretchable structure 20X is applicable not only to an underpants-type disposable diaper but also to other stretchable portions such as a lower torso or a fastening tape of a tape-type disposable diaper, a three-dimensional gather widely used for a general absorbent article, and a planar gather. In the illustrated example, the stretchable direction is set to the width direction, but can also be set to both the width direction and the front-back direction.

<Explanation of Terms in Specification>

The following terms in the specification have the following meanings unless otherwise specified in the specification.

"Front body" and "back body" mean a front portion and a back portion with the center of an underpants-type disposable diaper in the front-back direction as a boundary, respectively. A crotch portion means a front-back direction range including the center of an underpants-type disposable diaper in the front-back direction. When an absorber has a narrowing portion, the crotch portion means a front-back direction range of the portion having the narrowing portion.

"Elastic limit elongation" means stretch at an elastic limit in the stretchable direction ED (in other words, a state where the first sheet layer and the second sheet layer are completely unfolded), and represents the length at the elastic limit in terms of a percentage when a natural length is 100%.

"Area ratio" means the ratio of a target portion with respect to a unit area, and represents a ratio obtained by dividing the total area of a target portion (for example, bonded portions 40 and through-holes 31) in a target region (for example, stretchable region 80, non-stretchable region 70, main stretchable portion, and buffer stretchable portion) by the area of the target region in terms of a percentage. Particularly, "area ratio" in a region having a stretchable structure means an area ratio in a state where an article is stretched to an elastic limit in the stretchable direction ED. In a form in which many target portions are disposed at intervals, it is desirable to set a target region to a size including 10 or more target portions and to determine the area ratio.

"Stretch rate" means a value obtained when a natural length is 100%.

"Basis weight" is measured as follows. A sample or a test piece is predried and then left in a test chamber or an apparatus in a standard state (test location is at a temperature of 23±1° C. and a relative humidity of 50±2%) so as to have a constant weight. Predrying refers to causing a sample or a test piece to have a constant weight in an environment of a temperature of 100° C. Note that fibers having an official moisture regain of 0.0% do not have to be predried. A sample of 100 mm×100 mm in size is cut out from a test piece having a constant weight using a template for sampling (100 mm×100 mm). The weight of the sample is measured. The weight is multiplied by 100 to calculate the weight per square meter to be used as a basis weight.

The thickness of an absorber is measured by using a thickness meter (Peacock, dial thickness gauge large type, model J-B (measurement range: 0 to 35 mm) or model K-4 (measurement range: 0 to 50 mm)) manufactured by Ozaki Mfg. Co., Ltd. and making the sample and the thickness meter horizontal.

"Thickness" other than the above is automatically measured under conditions that a load is 0.098 N/cm$^2$ and a pressing area is 2 cm$^2$ using an automatic thickness meter (KES-G5 handy compression measuring program).

"Tensile strength" and "tensile elongation (breaking elongation)" mean values measured by setting an initial chuck interval (distance between marked lines) to 50 mm and setting a tensile speed to 300 mm/min according to JIS K7127: 1999 "Plastics—Test method for tensile properties—" except that a test piece has a rectangular shape with a width of 35 mm and a length of 80 mm.

"Stretch stress" means a tensile stress (N/35 mm) measured at the time of stretch in an elastic region by a tensile test in which an initial chuck interval (distance between marked lines) is set to 50 mm and a tensile speed is set to 300 mm/min according to JIS K7127: 1999 "Plastics—Test method for tensile properties—". The degree of stretch can be determined appropriately depending on a test target. A test piece preferably has a rectangular shape with a width of 35 mm and a length of 80 mm or more. However, if a test piece with a width of 35 mm cannot be cut out, a test piece with a width that can be cut out is prepared, and a value obtained by converting a measured value into a value with a width of 35 mm is used. Even when a target region is small as in an elastic film built into a product or a sufficiently large test piece cannot be collected, if the magnitude of a stretch stress is compared, at least comparison is possible appropriately even with small test pieces as long as the test pieces have the same size.

"Unfolded state" means a flatly unfolded state without contraction or slackness.

The size of each portion means a size not in a natural length state but in an unfolded state unless otherwise specified.

In a case where environmental conditions in a test and a measurement are not described, the test and the measurement are performed in a test room or an apparatus in a standard state (test location is at a temperature of 23±1° C. and a relative humidity of 50±2%).

INDUSTRIAL APPLICABILITY

The present invention can be used for a general disposable wearable article with a stretchable region, for example, various disposable diapers such as tape-type and pad-type disposable diapers or a sanitary napkin, in addition to an underpants-type disposable diaper as in the above example.

REFERENCE SIGNS LIST

10 Inner member
10B Inner and outer fixed region
11 Top sheet
12 Liquid impervious sheet
13 Absorber
13N Narrowing portion
14 Wrapping sheet
17 Non-absorber side portion
20 Outer member
20A First sheet layer
20B Second sheet layer
20C Folded-back portion
20X Elastic film stretchable structure
21 Side seal portion
23 Waist portion
24 Waist portion elastic member
25 Contraction wrinkles
30 Elastic film
31 through-hole
40 Bonded portion
70 Non-stretchable region
80 Stretchable region
90 Three-dimensional gather
93 Fallen portion
94 Free portion
95 Gather sheet
96 Elastically stretchable gather member
B Back body
ED Stretchable direction
F Front body
L Intermediate portion
LD Front-back direction
T Lower torso portion
WD Width direction
XD Orthogonal direction
33 Overlapping portion
26 First region
27 Second region

The invention claimed is:

1. A disposable wearable article comprising an elastic film stretchable structure in which a plurality of elastic films comprising a first elastic film and a second elastic film are laminated between a first sheet layer and a second sheet layer, and the first sheet layer and the second sheet layer are bonded to each other through holes passing through the plurality of elastic films or via the plurality of elastic films with many bonded portions arranged at intervals, wherein:
a region having the elastic film stretchable structure includes a stretchable region that elastically stretches and contracts together with the plurality of elastic films,
the stretchable region includes the plurality of elastic films disposed so as to have an overlapping portion,
a number of laminated layers of the plurality of elastic films in a first region of the stretchable region in an orthogonal direction orthogonal to a stretchable direction is more than that in each of second regions adjacent to both sides of the first region,
the first elastic film extends from one of the second regions to the first region,
the second elastic film extends from the other second region to the first region as the elastic film, wherein the one of the second regions includes only the first elastic film as the elastic film, the other second region includes only the second elastic film as the elastic film, and the first region includes the first elastic film and the second elastic film as the elastic film,
each of the first region and the second regions has the many bonded portions arranged at intervals, and
the many bonded portions are disposed in a same two-dimensional planar arrangement from the first region to the second regions.

2. The disposable wearable article according to claim 1, wherein an elongation at elastic limit of the one of second regions is different from that of the other second region, and the larger elongation at elastic limit thereof is the same as the elongation at elastic limit of the first region.

3. The disposable wearable article according to claim 1, wherein a stretch stress at the time of 4-times stretch in the stretchable direction in the first elastic film is different from a stretch stress at the time of 4-times stretch in the stretchable direction in the second elastic film.

4. The disposable wearable article according to claim 3, wherein an elongation at elastic limit of the one of the second regions is different from that of the other second region, and the larger elongation at elastic limit thereof is the same as the elongation at elastic limit of the first region.

5. The disposable wearable article according to claim 1, which is an underpants-type disposable wearable article comprising:
a front-back separated or front-back integrated outer member including a front body torso portion, a back body torso portion, and an intermediate portion located therebetween; and
an inner member attached to the outer member extending from the front body to the back body via a crotch portion, wherein both sides of the outer member in the front body are bonded to both sides of the outer member in the back body to form a side seal portion and to form a waist opening and a pair of left and right leg openings, and
at least one of the outer member of the front body and the outer member of the back body has the stretchable region that stretches and contracts in a width direction.

6. The disposable wearable article according claim 2, which is an underpants-type disposable wearable article comprising:
a front-back separated or front-back integrated outer member including a front body torso portion, a back body torso portion, and an intermediate portion located therebetween; and
an inner member attached to the outer member and extending from the front body to the back body via a crotch portion, wherein both sides of the outer member in the front body are bonded to both sides of the outer member in the back body to form a side seal portion and to form a waist opening and a pair of left and right leg openings, and
at least one of the outer member of the front body and the outer member of the back body has the stretchable region that stretches and contracts in a width direction.

7. The disposable wearable article according to claim 3, which is an underpants-type disposable wearable article comprising:
a front-back separated or front-back integrated outer member including a front body torso portion, a back body torso portion, and an intermediate portion located therebetween; and an inner member attached to the outer member and extending from the front body to the back body via a crotch portion, wherein both sides of the outer member in the front body are bonded to both sides of the outer member in the back body to form a side seal portion and to form a waist opening and a pair of left and right leg openings, and at least one of the outer member of the front body and the outer member of the back body has the stretchable region that stretches and contracts in a width direction.

8. A disposable wearable article comprising an elastic film stretchable structure in which a plurality of elastic films are laminated between a first sheet layer and a second sheet layer, and the first sheet layer and the second sheet layer are bonded to each other through holes passing through the plurality of elastic films or via the plurality of elastic films with many bonded portions arranged at intervals, wherein:

the elastic film stretchable structure includes a stretchable region that elastically stretches and contracts together with the plurality of elastic films, the disposable wearable article is an underpants-type disposable wearable article, both sides of an outer member in a front body are bonded to both sides of the outer member in a back body to form a side seal portion and to form a waist opening and a pair of left and right leg openings, the outer member includes a front body torso portion and a back body torso portion, each of the front body torso portion and the back body torso portion includes a waist portion comprising a waist portion elastic member, the waist portion elastic member is a plurality of elongated elastic members disposed at intervals in a front-back direction, an inner member is attached to the outer member and extending from the front body to the back body via a crotch portion, the inner member extending from the front body torso portion to the back body torso portion includes an absorber comprising a front edge disposed away from the waist portion of the front body toward the crotch portion and a back edge disposed away from the waist portion of the back body toward the crotch portion, at least one of the outer member of the front body and the outer member of the back body has the stretchable region, the stretchable region includes the plurality of elastic films disposed so as to have an overlapping portion, a number of laminated layers of the plurality of elastic films in a first region located in an intermediate portion of the stretchable region in an orthogonal direction orthogonal to a stretchable direction is different from that in each of second regions adjacent to both sides of the first region, one of the second regions includes only a first elastic film, the other second region includes only a second elastic film, and the first region includes the first elastic film and the second elastic film, each of the first elastic film and the second elastic film extends from one of the side seal portions to the other side seal portion, and the stretchable region includes the first region only where the first region is disposed between a line consisting of an edge of the absorber on the waist portion side and linearly extending lines from the both ends of the edge outwardly in a width direction, and the waist portion.

9. A disposable wearable article comprising an elastic film stretchable structure in which a plurality of elastic films are laminated between a first sheet layer and a second sheet layer, and the first sheet layer and the second sheet layer are bonded to each other through holes passing through the plurality of elastic films or via the plurality of elastic films with many bonded portions arranged at intervals, wherein:

the elastic film stretchable structure includes a stretchable region that elastically stretches and contracts together with the plurality of elastic films, the disposable wearable article is an underpants-type disposable wearable article, wherein both sides of an outer member in a front body are bonded to both sides of the outer member in a back body to form a side seal portion and to form a waist opening and a pair of left and right leg openings, the outer member includes a front body torso portion, a back body torso portion, an inner member is attached to the outer member and extending from the front body to the back body via a crotch portion, the outer member of the front body and the outer member of the back body each have the stretchable region, the stretchable region of the front body and the stretchable region of the back body include the plurality of elastic films disposed so as to have an overlapping portion, a number of laminated layers of the plurality of elastic films in a first region located in an intermediate portion of the stretchable region of the front body and the stretchable region of the back body in an orthogonal direction orthogonal to a stretchable direction is different from that in each of second regions adjacent to both sides of the first region, the plurality of elastic films include a first elastic film extending from one of the second regions to the first region, and a second elastic film extending from the other second region to the first region as the elastic film, the one of the second regions includes only the first elastic film as the elastic film, the other second region includes only the second elastic film as the elastic film, the first region includes the first elastic film and the second elastic film as the elastic film, each of the first elastic film and the second elastic film extends from one of the side seal portions to the other side seal portion, and the side seal portions do not include a portion that the first region of the front body and the first region of the back body overlap.

10. The disposable wearable article according to claim 9, wherein in the first elastic film and the second elastic film, a stretch stress at the time of 4-times stretch in the stretchable direction in the elastic film on the waist opening side is weaker than that in the elastic film on the opposite side.

* * * * *